(12) United States Patent
Boettger et al.

(10) Patent No.: US 9,271,993 B2
(45) Date of Patent: Mar. 1, 2016

(54) TREATMENT OF BACTERIAL INFECTIOUS DISEASES

(75) Inventors: Erik Boettger, Zürich (CH); Andrea Vasella, Zürich (CH)

(73) Assignees: UNIVERSITY OF ZURICH, Zurich (CH); ETH ZURICH, Zurich (CH)

( * ) Notice: Subject to any disclaimer, the term of this patent is extended or adjusted under 35 U.S.C. 154(b) by 0 days.

(21) Appl. No.: 13/820,258

(22) PCT Filed: Sep. 12, 2011

(86) PCT No.: PCT/EP2011/065701
§ 371 (c)(1),
(2), (4) Date: Mar. 1, 2013

(87) PCT Pub. No.: WO2012/034955
PCT Pub. Date: Mar. 22, 2012

(65) Prior Publication Data
US 2013/0165397 A1    Jun. 27, 2013

(30) Foreign Application Priority Data

Sep. 13, 2010 (EP) .................................. 10176317

(51) Int. Cl.
*A61K 31/7036* (2006.01)
*C07H 15/224* (2006.01)
*A61K 31/70* (2006.01)
*C07H 17/04* (2006.01)

(52) U.S. Cl.
CPC ............ *A61K 31/70* (2013.01); *A61K 31/7036* (2013.01); *C07H 15/224* (2013.01); *C07H 17/04* (2013.01)

(58) Field of Classification Search
CPC .......................... A61K 31/7036; C07H 15/224
See application file for complete search history.

(56) References Cited

U.S. PATENT DOCUMENTS

| | | | |
|---|---|---|---|
| 3,691,279 A | 9/1972 | Thompson et al. | |
| 3,876,767 A | 4/1975 | Ose | |
| 4,360,665 A | 11/1982 | Kirst | |
| 4,370,475 A * | 1/1983 | Igarashi et al. | 536/16.8 |
| 4,458,065 A * | 7/1984 | Kirst | 536/16.8 |
| 4,468,512 A * | 8/1984 | Kirst et al. | 536/16.8 |
| 4,468,513 A * | 8/1984 | Kirst et al. | 536/16.8 |
| 6,987,094 B2 * | 1/2006 | Malvolti et al. | 514/40 |

OTHER PUBLICATIONS

International Search Report issued Oct. 31, 2011 in International (PCT) Application No. PCT/EP2011/065701.
"Committee for Veterinary Medicinal Products Apramycin", The European Agency for the Evaluation of Medicinal Products, *Veterinary Medicines Evaluation Unit*, Jan. 1999.
J. Kondo et al., "Crystal Structure of the *Homo sapiens* Cytoplasmic Ribosomal Decoding Site Complexed with Apramycin", Angew. Chem. Int. Ed., vol. 45, pp. 3310-3314, 2006.
Matt, et al., "Dissociation of Antibacterial Activity and Aminoglycoside Ototoxicity in the 4-Monosubstitued 2-Deoxystreptamine Apramycin", PNAS, 2012, vol. 109, No. 27, p. 10984-10989.
"Matt et al. 10.1073/pnas.1204073109", PNAS, 2012, Supporting Information 27100, eleven (11) pages.
European Patent Application No. 11754424.7, Minutes of the Oral Proceedings before the Examining Division dated Jan. 26, 2015, three (3) pages.
Erik Christian Bottger, "Curriculum Vitae", 2014, twenty-one (21) pages.

* cited by examiner

*Primary Examiner* — Layla Bland
(74) *Attorney, Agent, or Firm* — Nath, Goldberg & Meyer; Tanya E. Harkins

(57) ABSTRACT

Novel pharmacological treatment of bacterial infectious diseases in humans by use of apramycin of formula (I) or apramycin derivatives having significantly low toxicity.

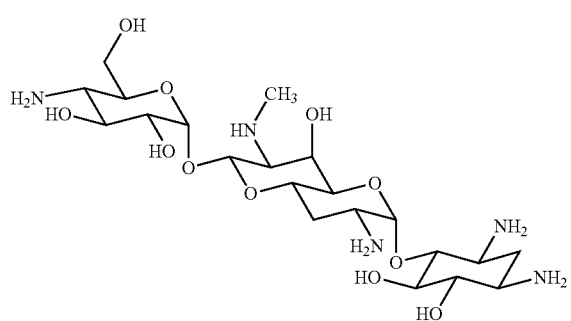

(I)

12 Claims, 2 Drawing Sheets a b

TREATMENT OF BACTERIAL INFECTIOUS DISEASES

This application is §371 national stage application of international application no. PCT/EP2011/065701 filed on Sep. 12, 2011.

FIELD OF THE INVENTION

The present invention relates to a novel pharmacological treatment of bacterial infectious diseases in humans. Specifically the invention relates to the use of apramycin and apramycin derivatives to treat bacterial infectious diseases in humans.

BACKGROUND OF THE INVENTION

Apramycin is an aminoglycoside antibiotic, originally named nebramycin factor II (U.S. Pat. No. 3,691,279). Its use in veterinary medicine has been disclosed in U.S. Pat. No. 3,876,767. Apramycin and some acylated or alkylated derivatives thereof have been further described as broad spectrum antibiotics in U.S. Pat. No. 4,360,665. Apramycin, however, has never been used in humans because it is thought to have a relatively high risk of toxicity (Kondo et al., Angew. Chem. Int. Ed. 2006, 45: 3310-3314). Apramycin is not even authorised for use in cattle or sheep producing milk for human consumption.

SUMMARY OF THE INVENTION

The present invention provides a method of treating bacterial infectious diseases in humans, comprising administering to a patient in need thereof a therapeutically effective amount of apramycin of formula (I) or of an apramycin derivative.

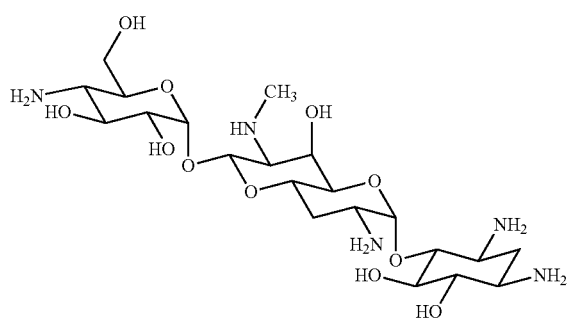

(I)

Furthermore the invention relates to apramycin or an apramycin derivative for use in such a treatment, to the use of apramycin or of an apramycin derivative for the manufacture of a medicament for the treatment of bacterial infectious diseases in humans, and to some particular new apramycin derivatives.

A=Control

B=Apramycin 0.5 mM: little (<5%) inner and outer hair cells are missing.

C=Gentamicin 0.5 mM: all (>80%) inner and outer hair cells are lost.

D=Neomycin 0.5 mM: all (>80%) inner and outer hair cells are lost.

Figure 2:
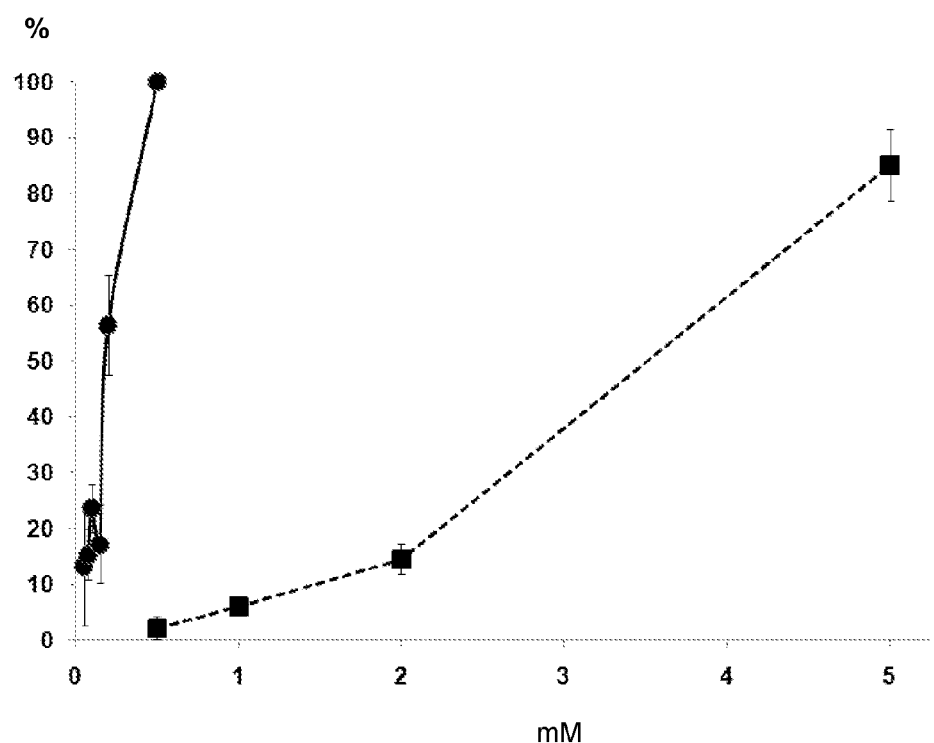
Figure 2:
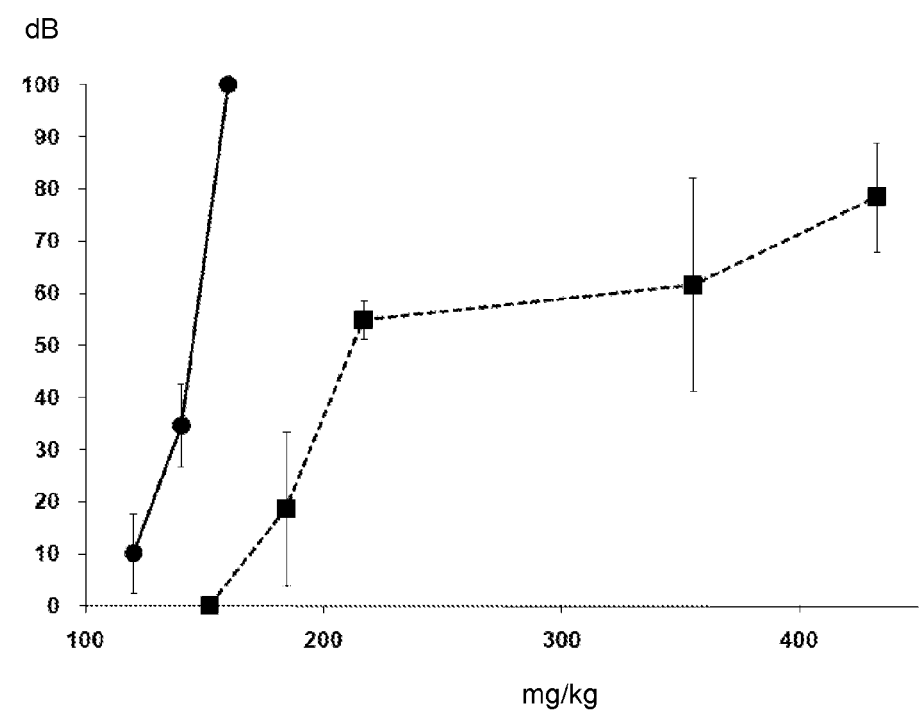

FIG. 2: Hair cell loss in cochlear explants and ototoxicity in vivo (a) Dose-response relationship of drug-induced hair cell loss in cochlear explants. Hair cell loss was quantified along the entire length of the explant and plotted against drug concentration. %=% outer hair cells missing.

Circles ● and solid line ---: gentamicin; squares ■ and dotted line -----: apramycin. Data points represent means±sem, n=3 to 12 per data point.

(b) Effect of chronic aminoglycoside treatment in vivo on auditory brain stem response. dB=threshold shift at 12 kHz. "Treshold shift" is the difference in auditory threshold before and three weeks after treatment.

Circles ● and solid line ---: gentamicin; squares and dotted line -----: apramycin. Data points represent means±sem, n=3 to 11 per data point (except for 160 mg gentamicin with only 1 surviving animal). Note that the threshold shift is given in dB, which corresponds to a logarithmic scale, i.e. every 10 dB indicates a 1 $\log_{10}$ difference in energy.

In vitro cochleatoxicity of apramycin is significantly less than that of gentamicin and the in vivo auditory response is substantially less affected following apramycin treatment compared to gentamicin.

DETAILED DESCRIPTION OF THE INVENTION

The present invention provides a method of treating bacterial infectious diseases in humans. The inventive treatment comprises administering to a patient in need thereof a therapeutically effective amount of apramycin or of an apramycin derivative, or of an acid addition salt thereof, in particular a therapeutically effective amount of apramycin or of an acid addition salt thereof.

Furthermore the invention relates to apramycin or an apramycin derivative, or an acid addition salt thereof, for use in the treatment of bacterial infectious diseases in humans, and to the use of apramycin or of an apramycin derivative, or of an acid addition salt thereof, for the manufacture of a medicament for the treatment of bacterial infectious diseases in humans. Preferably, apramycin or an acid addition salt thereof is used.

It is demonstrated that apramycin surprisingly does not have the expected high level of toxicity observed with related aminoglycoside antibiotics, but actually is significantly less toxic than compounds already used in human medicine such as gentamicin.

Apramycin is the aminoglycoside of formula (I)

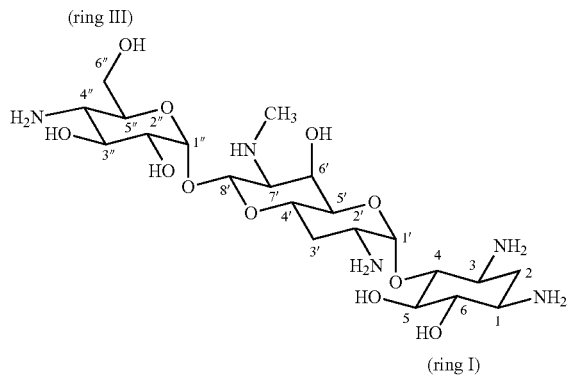

(I)

A derivative of apramycin according to the invention is, for example, a derivative of an apramycin of formula (I) wherein
- one or more amino groups are alkylated, cycloalkylated, alkenylated and/or acylated, or replaced by a hydroxy group, and/or
- one or more hydroxy groups are alkylated, alkenylated, acylated, and/or replaced by an amino group, and/or
- two neighbouring hydroxy groups are cyclized to form an acetal or a carbonate, and/or
- a neighbouring hydroxy group and an amino group or an N-acylated amino group are cyclized to form an aminoacetal or a carbamate, and/or
- the 7'-NHCH$_3$ group is replaced by an amino group NH$_2$, an alkylated, cycloalkylated, alkenylated and/or acylated amino group, a hydroxy group, an alkylated, cycloalkylated, alkenylated or acetylated hydroxy group, and/or
- the 3' carbon atom is substituted by an amino group NH$_2$ or an alkylated, cycloalkylated, alkenylated and/or acylated amino group, or by a hydroxy group OH or an alkylated, alkenylated or acylated hydroxy group, and/or
- the 5 and/or the 6 hydroxy group is glycosylated by a monosaccharide, and/or
- ring I or ring III is replaced by a different monosaccharide.

Alkyl groups considered for the alkylation of a hydroxy group and/or of an amino group are linear or branched $C_1$-$C_7$-alkyl, preferably $C_1$-$C_4$-alkyl, for example methyl, ethyl, n-propyl, isopropyl or isobutyl, in particular methyl or ethyl; cyclopropylmethyl, optionally substituted benzyl, for example benzyl or p-methoxybenzyl; and amino-, acetylamino- and/or hydroxy-$C_1$-$C_4$-alkyl, for example 2-aminoethyl, 2-acetylaminoethyl, 2-hydroxyethyl, 4-amino-2-hydroxybutyl, or 3-amino-2-hydroxypropyl.

Cycloalkyl groups considered for the cycloalkylation of an amino group are $C_3$-$C_7$-cycloalkyl, in particular cyclopropyl.

Alkenyl groups considered for the alkenylation of a hydroxy group and/or of an amino group are linear or branched $C_1$-$C_7$-alkenyl, preferably $C_1$-$C_4$-alkenyl, for example allyl or isobutenyl, in particular allyl.

Acyl groups considered for the acylation of a hydroxy group and/or an amino group are $C_1$-$C_7$-acyl, preferably $C_1$-$C_4$-acyl, for example ethoxycarbonyl, propionyl or acetyl, in particular acetyl; amino-, acetylamino- and/or hydroxy-$C_1$-$C_7$-acyl, for example hydroxyacetyl, aminoacetyl, acetylaminoacetyl, γ-amino-α-hydroxybutyryl, γ-acetylamino-α-hydroxybutyryl, β-amino-α-hydroxypropionyl, or β-acetylamino-α-hydroxypropionyl; aminoacetyl groups derived from the 20 naturally occurring essential α-amino acids, preferably derived from neutral or basic α-amino acids, for example derived from alanine, valine, leucine, isoleucine, serine, threonine, phenylalanine or lysine; aroyl, for example optionally substituted benzoyl, such as benzoyl, p-methoybenzoyl or 3,4,5-trimethoxybenzoyl; and heteroaroyl, for example pyridylcarbonyl, such as 2-, 3- or 4-pyridylcarbonyl, thiophenecarbonyl, such as 2- or 3-thiophenecarbonyl, or furanylcarbonyl, such as 2- or 3-furanylcarbonyl. Further acyl groups considered for the acylation of a hydroxy group are sulfate and phosphate esters.

A cyclic acetal formed from two neighbouring hydroxyl groups is an acetal derived from a $C_1$-$C_7$-alkylcarbaldehyde, preferably $C_1$-$C_4$-alkylcarbaldehyde, for example formaldehyde, acetaldehyde, benzaldehyde, a di($C_1$-$C_7$-alkyl)ketone, preferably di($C_1$-$C_4$-alkyl)ketone, for example acetone, from cyclopentanone, or from cyclohexanone. A cyclic aminoacetal formed from a neighbouring hydroxy group and an amino group is likewise derived from a $C_1$-$C_7$-alkylcarbaldehyde, benzaldehyde, a di($C_1$-$C_7$)ketone, cyclopentanone, or cyclohexanone; it may be N-acylated by $C_1$-$C_4$ acyl groups.

In substituted benzyl and substituted benzoyl, the substituent may be $C_1$-$C_4$-alkyl, for example methyl, $C_1$-$C_4$-alkoxy, for example methoxy or ethoxy, chloro, bromo, fluoro, cyano, or nitro. Such substituted benzyl or benzoyl may carry one, two or three of the mentioned substituents.

A monosaccharide considered as replacement of ring I or ring III or as a substituent of the 5 or 6 hydroxy group is, for example, glucose, glucosamine, 3-amino-3-deoxyglucose, 3,4-diamino-3,4-dideoxyglucose, 4-amino-3,4dideoxyglucose, 4-amino-3,6-dideoxyglucose, 6-amino-6-deoxyglucose, 4-amino-4-deoxyallose, 4-amino-4-deoxyidose, ribose, 5-amino-5-deoxyribose, 3,5-diamino-3,5-dideoxyribose, xylose, 5-amino-5-deoxyxylose, 3,5-diamino-3,5-dideoxyxylose, arabinose, 4-amino-4-deoxy arabinose (D and L), 5-amino-5-deoxy arabinose, 3,5-diamino-3,5-dideoxy arabinose, 6-amino-3,4,6-trideoxy-D-erythro-hex-3-enopyranose, or 6-amino-4,5,6-trideoxy-L-threo-hex-4-enopyranose Any amino group of apramycin or an amino group of a substituent amino-alkyl or amino-acyl may be in protected form. Protecting groups considered are, for example, those mentioned in books on protective groups such as T. W. Greene and P. G. M. Wuts, "Protective Groups in Organic Synthesis", Wiley, 3$^{rd}$ edition 1999. Particular examples of protecting groups for amino groups are phthaloyl, succinoyl, glutaroyl, tert-butoxycarbonyl, benzoxycarbonyl, and the like.

Particular derivatives of apramycin are derivatives of formula (I) wherein
- one or more amino groups are alkylated, cycloalkylated, alkenylated and/or acylated and/or
- one or more hydroxy groups are alkylated, alkenylated or acylated, and/or
- two neighbouring hydroxy groups are cyclized to form an acetal or a carbonate, and/or
- a neighbouring hydroxy group and amino group are cyclized to form an aminoacetal or a carbamate, and/or
- the 7'-NHCH$_3$ group is replaced by an amino group NH$_2$ or an alkylated, cycloalkylated, alkenylated and/or acylated amino group, and/or
- the 3' carbon atom is substituted by an amino group NH$_2$ or an alkylated, cycloalkylated, alkenylated and/or acylated amino group, or by a hydroxy group OH or an alkylated, alkenylated or acylated hydroxy group.

More specifically a derivative of apramycin is a compound of formula (II),

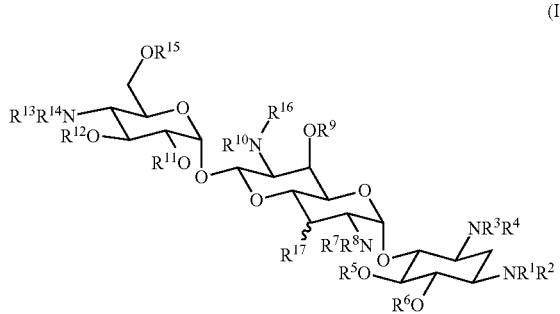

(II)

wherein $R^1$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^2$ is hydrogen, $C_1$-$C_4$-alkyl, or $C_1$-$C_4$-alkenyl;

$R^3$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^4$ is hydrogen, $C_1$-$C_4$-alkyl, or $C_1$-$C_4$-alkenyl;

$R^5$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, a monosaccharide derived from naturally occurring pentoses and hexoses and the corresponding monamino-deoxy or diamino-didedoxy derivatives, aroyl, heteroaroyl, $SO_2OH$, or $PO(OH)_2$;

$R^6$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, a monosaccharide derived from naturally occurring pentoses and hexoses and the corresponding monamino-deoxy or diamino-didedoxy derivatives, aroyl, heteroaroyl, $SO_2OH$, or $PO(OH)_2$; or $R^1$ and $R^6$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O; or $R^5$ and $R^6$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^7$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^8$ is hydrogen, $C_1$-$C_4$-alkyl, or $C_1$-$C_4$-alkenyl;

$R^9$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^{10}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^9$ and $R^{10}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{11}$ is hydrogen, $C_1$-$C_7$-alkyl, cyclopropylmethyl, optionally substituted benzyl, amino-$C_1$-$C_7$-acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^{12}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{11}$ and $R^{12}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{13}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{12}$ and $R^{13}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{14}$ is hydrogen, $C_1$-$C_4$-alkyl, or $C_1$-$C_4$-alkenyl;

$R^{15}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{13}$ and $R^{15}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{16}$ is hydrogen, $C_1$-$C_4$-alkyl, cyclopropylmethyl, cyclopropyl, or $C_1$-$C_4$-alkenyl; or, optionally, N—$R^{10}$ and $R^{16}$ together represent a saturated or partially unsaturated heterocycle, such as aziridine, azetidine, pyrrolidine, piperidine, piperazine, or morpholine; and $R^{17}$ is hydrogen; amino, $C_1$-$C_7$-alkylamino, cyclopropylmethylamino, optionally substituted benzylamino, amino-$C_1$-$C_7$-alkylamino, acetylamino-$C_1$-$C_7$-alkylamino, hydroxy-$C_1$-$C_7$-alkylamino, amino-hydroxy-$C_1$-$C_7$-alkylamino, acetylamino-hydroxy-$C_1$-$C_7$-alkylamino, $C_3$-$C_7$-cycloalkylamino, $C_1$-$C_4$-alkenylamino, $C_1$-$C_7$-acylamino, amino-$C_1$-$C_7$-acylamino, acetylamino-$C_1$-$C_7$-acylamino, hydroxy-$C_1$-$C_7$-acylamino, amino-hydroxy-$C_1$-$C_7$-acylamino, acetylamino-hydroxy-$C_1$-$C_7$-acylamino, aminoacetylamino, wherein aminoacetyl is derived from the 20 naturally occurring essential α-amino acids, aroylamino, heteroaroylamino, $NHSO_2OH$, $NHPO(OH)_2$; hydroxy, $C_1$-$C_7$-alkoxy, cyclopropylmethoxy, optionally substituted benzyloxy, amino-$C_1$-$C_7$-alkoxy, acetylamino-$C_1$-$C_7$-alkoxy, hydroxy-$C_1$-$C_7$-alkoxy, amino-hydroxy-$C_1$-$C_7$-alkoxy, acetylamino-hydroxy-$C_1$-$C_7$-alkoxy, $C_1$-$C_4$-alkenyloxy, $C_1$-$C_7$-acyloxy, amino-$C_1$-$C_7$-acyloxy, acetylamino-$C_1$-$C_7$-acyloxy, hydroxy-$C_1$-$C_7$-acyloxy, amino-hydroxy-$C_1$-$C_7$-acyloxy, acetylamino-hydroxy-$C_1$-$C_7$-acyloxy, aminoacetoxy wherein aminoacetyl is derived from the 20 naturally occurring essential α-amino acids, aroyloxy, heteroaroyloxy, $OSO_2OH$, or $OPO(OH)_2$;

with the proviso, that when $R^{16}$ is methyl and $R^{17}$ is hydrogen, at least one of the substituents $R^1$ to $R^{15}$ is different from hydrogen;

and derivatives thereof, wherein one or more amino group are in protected form.

Preferred are compounds of formula (II) wherein $R^{17}$ is hydrogen. In such compounds, any of the 5 secondary hydroxy groups and the one primary hydroxy group ($OR^{15}$) may be alkylated, alkenylated or acylated, or replaced by a hydrogen atom, or also 2, 3, 4, 5, or all 6 hydroxy groups.

Preferred are compounds of formula (II) wherein one of $R^5$, $R^6$, $R^9$, $R^{11}$, $R^{12}$ and $R^{15}$, in particular $R^{15}$, is $C_1$-$C_4$-alkyl, for example methyl, or $C_1$-$C_4$-acyl, for example acetyl, $R^{16}$ is methyl, and the other substituents are all hydrogen. Likewise preferred is the compound wherein all of $R^5$, $R^6$, $R^9$, $R^{11}$, $R^{12}$ and $R^{15}$ are $C_1$-$C_4$-alkyl, for example methyl, or $C_1$-$C_4$-acyl, for example acetyl, $R^{16}$ is methyl, and the other substituents are all hydrogen.

Preferred is a derivative wherein $R^{15}$ is $C_1$-$C_4$-alkyl, $C_1$-$C_4$-alkenyl or $C_1$-$C_4$-acyl, $R^{16}$ is methyl, and all other substituents are hydrogen. Also preferred is a derivative wherein one, two or three out of $R^5$, $R^6$ and $R^{12}$ are $C_1$-$C_4$-alkyl, $C_1$-$C_4$-alkenyl or $C_1$-$C_4$-acyl, $R^{16}$ is methyl, and all other substituents are hydrogen.

Likewise, in compounds of formula (II) wherein $R^{17}$ is hydrogen, any of the 4 primary amino groups may be alkylated, dialkylated, alkenylated, dialkenylated or acylated, or also 2, 3, or all 4 primary amino groups, for example in the form of the tetraacetate.

Preferred are compounds of formula (II) wherein one of $R^1$, $R^3$, $R^7$ and $R^{13}$, in particular $R^{13}$, is $C_1$-$C_4$-alkyl, for example methyl, $C_3$-$C_7$-cycloalkyl, for example cyclopropyl, $C_1$-$C_4$-acyl, for example acetyl, amino-, acetylamino- and/or hydroxy-$C_1$-$C_4$-acyl, for example hydroxyacetyl, aminoacetyl, acetylaminoacetyl, γ-amino-α-hydroxybutyryl, γ-acetylamino-α-hydroxybutyryl, β-amino-α-hydroxypropionyl, or β-acetylamino-α-hydroxypropionyl, $R^{16}$ is methyl, and the other substituents are all hydrogen. Likewise preferred is the compound wherein all of $R^1$, $R^3$, $R^7$ and $R^{13}$ are $C_1$-$C_4$-acyl, for example acetyl, $R^{16}$ is methyl, and the other substituents are all hydrogen. Likewise preferred are compounds, wherein the amino group of such preferred substituent aminoacetyl, γ-amino-α-hydroxybutyryl, or β-amino-α-hydroxypropionyl is in protected form, e.g. protected with benzoxycarbonyl or phthaloyl.

The secondary amino group $NR^{10}R^{16}$, wherein $R^{16}$ is $CH_3$, may be alkylated by a second methyl group ($R^{10}$ is $CH_3$), by a cyclopropylmethyl ($R^{10}$ is cyclo-$C_3H_5$—$CH_2$—) or a cyclopropyl group ($R^{10}$ is cyclo-$C_3H_5$—), alkenylated by an allyl group ($R^{10}$ is $CH_2$=$CHCH_2$—) or acetylated ($R^{10}$ is $CH_3CO$—). Optionally, $NR^{10}R^{16}$ may also represent a saturated or partially unsaturated heterocycle, such as aziridine, azetidine, pyrrolidine, piperidine, piperazine, or morpholine.

Preferred are compounds of formula (II), wherein $R^1$ or $R^7$ or $R^{13}$, in particular $R^{13}$, is amino-, acetylamino- and/or hydroxy-$C_1$-$C_7$-acyl, for example hydroxyacetyl, aminoacetyl, acetylaminoacetyl, γ-amino-α-hydroxybutyryl, γ-acetylamino-α-hydroxybutyryl, β-amino-α-hydroxypropionyl, or β-acetylamino-α-hydroxypropionyl, $R^{16}$ is methyl, and all other substituents are hydrogen.

Likewise preferred are compounds of formula (II), wherein $R^9R^{10}$ is C=O, $R^{13}$ is amino-, acetylamino- and/or hydroxy-$C_1$-$C_7$-acyl, for example hydroxyacetyl, aminoacetyl, acetylaminoacetyl, γ-amino-α-hydroxybutyryl, γ-acetylamino-α-hydroxybutyryl, β-amino-α-hydroxypropionyl, or β-acetylamino-α-hydroxypropionyl, $R^{16}$ is methyl, and all other substituents are hydrogen.

Further preferred are compounds of formula (II), wherein $R^{10}$ is methyl or allyl, $R^{16}$ is methyl, and all other substituents are hydrogen; or wherein $R^{16}$ is ethyl, cyclopropylmethyl, cyclopropyl, or allyl, and all other substituents are hydrogen.

Acid addition salts of apramycin are salts with organic or inorganic acids, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantane-carboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzene-sulfonic acid, methylsulfuric acid, ethylsulfuric acid, dodecylsulfuric acid, N-cyclohexyl-sulfamic acid, N-methyl-, N-ethyl- or N-propyl-sulfamic acid, or other organic protonic acids, such as ascorbic acid.

Apramycin derivatives as defined hereinbefore do not include derivatives, wherein amino or hydroxy groups are missing in position 5 and 6 in ring I of the apramycin structure as indicated in formula (I), or other derivatives having undergone further additions to the structure of apramycin except those indicated above, or eliminations or deletions of parts of the structure of apramycin.

Apramycin, an apramycin derivative, or an acid addition salt thereof is particularly active against bacteria and bacteria-like organisms. It is suitable in human medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis. Staphylococcus aureus, S. epidermidis*, or *S. haemolyticus*; pharyngitis, rheumatic fever, and glomerulonephritis related to infection by *Streptococcus pyogenes*, Groups C and G streptococci, or *Corynebacterium diphthenae*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, quinolones, chloramphenicol, tetracyclines and macrolides; skin and soft tissue infections and abscesses, and puerperal fever related to infection by *Staphylococcus aureus*, coagulase-negative staphylococci (e.g. *S. epidermidis, S. haemolyticus*), *Streptococcus pyogenes, Streptococcus agalactiae*, Streptococcal groups C—F (minute colony streptococci), viridans streptococci, *Corynebacterium minutissimum*, or *Bartonella henselae*; urinary tract infections related to infection by *Enterobacteriaceae* spp., *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes H influenzae*, or *Listeria* spp.; disseminated disease related to infection with non-tuberculous mycobacteria (NTM) such as *Mycobacterium avium-intracellulare, M. abscessus, M. bolletii*, or *M. massiliense*; infections caused by *Mycobacterium tuberculosis, M. leprae, M. paratuberculosis; M. kansasii, M. chelonei*, or *M. fortuitum*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; atherosclerosis or cardiovascular disease related to infection by *Helicobacter pylori* or *Chlamydia pneumonia*; and disseminated infections caused by *Francisella tularensis, Rickettsia* spp., *Brucella* spp., *Enterobacteriaceae*, and Gram-negative non-fermentive rods (e.g. *Pseudomonas* spp.).

Apramycin, an apramycin derivative, or an acid addition salt thereof is particularly useful in the treatment of pneumonia due to *Pseudomonas* spp. infection in cystic fibrosis patients, or disseminated infection to *Francisella tularensis, Rickettsia* spp., *Brucella* spp., *Enterobacteriaceae* spp., and *Pseudomonas* spp.

A particular bacterial infectious disease to be treated by apramycin, an apramycin derivative, or an acid addition salt thereof, is tuberculosis. A further particularly considered disease is septicemia caused by bacterial pathogens. A third particularly considered disease is pneumonia due to *Pseudomonas* spp. infection in cystic fibrosis patients. A fourth particularly considered disease is an infection due to non-tuberculous mycobacteria such as *M. avium-intracellulare, M. abscessus, M. bolletii*, or *M. massiliense*.

For the administration, the active ingredient is preferably in the form of a pharmaceutical preparation comprising apramycin, an apramycin derivative, or an acid addition salt thereof in chemically pure form, and optionally a pharmaceutically acceptable carrier and optionally adjuvants. Apramycin, the apramycin derivative, or the acid addition salt thereof is used in an amount effective against the bacterial infectious disease in humans. The dosage of the active ingredient depends upon the age, weight, and individual condition of the human being, the individual pharmacokinetic data, and the mode of administration. In the case of an individual human having a bodyweight of about 70 kg the daily dose administered of apramycin or a derivative thereof is from 0.01 mg/kg bodyweight to 1000 mg/kg bodyweight, preferred is from 0.1 mg/kg bodyweight to 100 mg/kg bodyweight, more preferred from 1 mg/kg to 25 mg/kg bodyweight administered as a single dose or as several doses. Apramycin, the derivative of apramycin, or the acid addition salt thereof can be used alone or in combinations with other drugs.

Pharmaceutical compositions for enteral administration, such as nasal, buccal, rectal or, especially, oral administration, and for parenteral administration, such as subcutaneous, intravenous, intrahepatic or intramuscular administration, are especially preferred. The pharmaceutical compositions comprise from approximately 1% to approximately 95% active ingredient, preferably from approximately 20% to approximately 90% active ingredient.

For parenteral administration preference is given to the use of solutions of apramycin, apramycin derivatives, or the acid addition salt thereof, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal/intraperitoneal and intravenous applications are also considered, for example using a transdermal patch, which allows administration over an extended period of time, e.g. from one to twenty days.

Applications as aerosols are likewise considered. The active ingredient is provided in solid form in a predetermined particle size or as a solution. Solids may be used admixed with suitable fillers, such as sugars, for example lactose. Solutions are preferably aqueous solutions, optionally containing preservatives, stabilizers, solubilizers, salts for regulating osmotic pressure and/or buffers. Aerosols are applied with the aid of suitable nebulizers, or optionally together with a propellant, for example HFA 134a (1,1,1,2,-tetrafluoroethane), HFA 227 (1,1,1,2,3,3,3-heptafluoropropane), dichlorodifluoromethane, 1,1- or 1,2-di-chlorotetrafluoroethane, trichlorofluoromethane, or combinations of thereof, in pressurized form.

Intravenous, intramuscular or subcutaneous applications are particularly preferred. In pneumonia due to *pseudomonas* spp. infection in cystic fibrosis patients application as an aerosol is particularly preferred.

Medicaments according to the invention are manufactured by methods known in the art, especially by conventional mixing, coating, granulating, dissolving or lyophilizing. Apramycin, an apramycin derivative, or the acid addition salt thereof can be administered alone or in combination with one or more other therapeutic agents, possible combination therapy taking the form of fixed combinations of apramycin or apramycin derivatives and one or more other therapeutic agents known in the treatment of bacterial infectious diseases in humans, the administration being staggered or given independently of one another, or being in the form of a fixed combination.

Possible combination partners considered are beta-lactams, macrolides, chinolones, rifamycins, or isoniazid.

The invention also relates to the new apramycin derivatives per se, and acid addition salts thereof. Particular compounds considered are
the compound of formula (II), wherein $R^1$ is γ-amino-α-hydroxybutyryl, $R^{16}$ is methyl, and all other substituents are hydrogen;
the compound of formula (II), wherein $R^7$ γ-amino-α-hydroxybutyryl, $R^{16}$ is methyl, and all other substituents are hydrogen; and
the compound of formula (II), wherein $R^9R^{10}$ is C=O, $R^{13}$ is γ-amino-α-hydroxybutyryl, $R^{16}$ is methyl, and all other substituents are hydrogen.

Further compounds considered are
the compound of formula (II), wherein $R^{10}$ is methyl, $R^{16}$ is methyl, and all other substituents are hydrogen;
the compound of formula (II), wherein $R^{10}$ is allyl, $R^{16}$ is methyl, and all other substituents are hydrogen;
the compound of formula (II), wherein $R^{16}$ is ethyl, and all other substituents are hydrogen;
the compound of formula (II), wherein $R^{16}$ is cyclopropylmethyl, and all other substituents are hydrogen;
the compound of formula (II), wherein $R^{16}$ is cyclopropyl, and all other substituents are hydrogen; and
the compound of formula (II), wherein $R^{16}$ is allyl, and all other substituents are hydrogen.

The following examples serve to illustrate the invention without limiting the invention in its scope.

The data show that apramycin exhibits potent antibacterial activity, including against *M. tuberculosis*, and that the antibacterial activity of apramycin is not compromised by many of the known aminoglycoside resistance determinants.

In particular, these data demonstrate:

i) The activity of apramycin for the bacterial ribosome is similar to that of tobramycin, gentamicin, neomycin and paromomycin. Compared to tobramycin, gentamicin, neomycin and paromomycin, apramycin shows significantly less activity for mutant bacterial ribosomes with single rRNA residues indicative of human sequence polymorphisms, e.g. 1408G, 1491A, 1491C. Compared to tobramycin, gentamicin, neomycin and paromomycin, apramycin shows significantly less activity for bacterial hybrid ribosomes carrying the humanized drug binding site, e.g. mitohybrid, cytohybrid, 1555G deafness, 1494U deafness (for underlying rationale and methodology see patent application WO 2007/112965; Hobbie et al., Nucl. Acids Res. 2007, 35: 6086-6093; Hobbie et al., Proc. Natl. Acad. Soc. USA 2008, 105: 20888-20893). Collectively, these data testify that selectivity at the drug target level, i.e. the distinction between prokaryotic and eukaryotic ribosomes (Bottger et al., EMBO Rep. 2001, 2: 318-323), is higher for apramycin than for other aminoglycosides.

ii) In comparison to gentamicin, apramycin surprisingly shows little cochlea toxicity in vitro (ex vivo cochlea organ cultures), less nephrotoxicity in vivo (guinea pig) and less ototoxicity in vivo (guinea pig). Accordingly apramycin is suitable for human use.

Example 1

Activity of Apramycin Against Clinical Methicillin Resistant *Staphylococcus aureus* (MRSA) Isolates in Comparison to Commercially Available Aminoglycosides (Table 1)

Activity was assessed by determination of minimal inhibitory concentrations (MIC), as described in Pfister et al., Antimicrob. Agents Chemother. 2003, 47:1496-1502. Cultures from single colonies were grown in LB medium and used for MIC tests in a microtiter plate format. Starting cultures contained 200 μl of bacterial cells at an optical density of 0.025 at 600 nm, and the respective drug was added in twofold series of dilution. The MIC was defined as the drug concentration at which the growth of the cultures was completely inhibited after 24 h of incubation at 25° C.

In contrast to the clinically well established aminoglycosides gentamicin, sisomicin, tobramycin, kanamycin, amikacin, neomycin and paromomycin, apramycin is not affected by any of the resistance determinants present in clinical MRSA isolates.

The results are shown in Table 1.

TABLE 1

Activity of apramycin against clinical methicillin resistant *Staphylococcus aureus* (MRSA) isolates in comparison to commercially available aminoglycosides—MICs (mg/l), LB microdilution assay

| No.[a] | Strain[b] | Apramycin | Gentamicin | Sisomicin | Tobramycin | Kanamicin A | Amikacin | Neomycin | Paromomycin |
|---|---|---|---|---|---|---|---|---|---|
| 38 | 70-26S | 8 | 0.5 | 0.25 | 0.5-1 | 4 | 4 | 0.5-1 | 2-4 |
| 41 | 98-25S | 8 | 0.5 | 0.25 | 0.5-1 | 2-4 | 4-8 | 0.5-1 | 4 |
| 40 | 87-26S | 8 | 0.5 | 0.25 | ≥256 | 128-256 | 16-32 | 128 | >256 |
| 44 | 07-12R | 16 | 16 | 8 | 8 | 64 | 4 | 0.5-1 | 2-4 |
| 45 | 08-12R | 8-16 | 16 | 4-8 | 8 | 64 | 4 | 0.5-1 | 4 |
| 43 | 01-08R | 16-32 | 32-64 | 32-64 | 32 | 128-256 | 8-16 | 1-4 | 4-8 |
| 53 | 56-06R | 8 | 64 | 32 | 16-32 | 256 | 8 | 0.5-1 | 2-4 |
| 42 | 101-06R | 8 | 32-64 | 32 | ≥256 | 256 | 16 | 128 | >256 |
| 46 | 12-06R | 8-16 | ≥256 | >256 | 128-256 | >256 | 32 | >256 | >256 |
| 47 | 18-06R | 8-16 | ≥256 | >256 | ≥256 | >256 | 256 | 256 | >256 |
| 48 | 20-06R | 8-16 | ≥256 | >256 | ≥256 | >512 | 256 | 256 | >256 |
| 49 | 23-12R | 8-16 | 16 | 8 | 8-16 | >256 | 8-16 | >256 | >256 |
| 50 | 31-06R | 4-8 | 128 | 128-256 | 32-64 | >256 | 16 | 64 | >256 |
| 51 | 36-06R | 8 | 128 | 64 | 32-64 | >256 | 8-16 | 64 | >256 |
| 52 | 53-14I | 8 | 16-32 | 8 | 8-16 | >256 | 16 | >256 | >256 |

[a]The full MSRA designation (No.) is AG038 etc. Only the last two digits are shown.
[b]The full strain designation is 70-26S Gm$^S$ etc. for strains ending with S, and 07-12R Gm$^R$ etc. for strains ending with R or I.

Example 2

Activity of Apramycin in Comparison to Commercially Available Aminoglycosides Against Gram-Negative Bacteria (Table 2)

Activity was assessed by determination of minimal inhibitory concentrations (MIC) as described in Example 1.

Compared to the heterogeneous activity profiles as observed for gentamicin, sisomicin, tobramycin, kanamycin, neomycin and paromomycin, apramycin shows a unique activity profile largely unaffected by the main aminoglycoside resistance determinants.

The results are shown in Table 2.

Example 3

Activity of Apramycin in Comparison to Amikacin and Streptomycin Against Clinical Isolates of *M. Tuberculosis* (Table 3)

Activity of apramycin (μg/ml) in comparison to amikacin and streptomycin against clinical isolates of *M. tuberculosis* was measured using MGIT960 EpiCenter instrumentation. R=resistant, S=susceptible; for methodology see Springer et al., J. Clin. Microbiol. 2009, 47:1773-1780. Results are shown in Table 3.

TABLE 2

Activity of apramycin in comparison to commercially available aminoglycosides against gram-negative bacteria as determined by minimal inhibitory concentrations (MICs, mg/l)

| No[a] | Strain[b] | RM[b] | Apramycin | Gentamicin | Sisomicin | Tobramycin | Kanamicin A | Neomycin | Paromomycin |
|---|---|---|---|---|---|---|---|---|---|
| 01 | clin. isol. (Gm$^S$) | — | 16 | 4-8 | — | 4-8 | 16 | 8-16 | 16-32 |
| 02 | clin. isol (Gm$^S$) | — | 16-32 | 2 | 1 | 2 | 4-8 | 4 | 8-16 |
| 03 | clin. isol (Gm$^R$) | — | 16-32 | 256-512 | 32-128 | 32 | 16-32 | 4 | 8-16 |
| 06 | BM13 | — | 4 | 0.5 | 0.25 | 0.5 | 1-2 | 1 | 2 |
| 07 | BM13/pIP135 | AAC(3) | 8 | 32-64 | 16 | 4 | 8 | 4 | 8 |
| 08 | BM13/pIP055 | ANT(2") | 4 | 16 | 8 | 8-64 | 16-128 | 2-4 | 4-8 |
| 09 | AAC(6')-1B | AAC(6') | 8 | 8-16 | 16 | 64-128 | 256-512 | 8-32 | 8-16 |
| 36 | HB101/pAT197 | ANT(4') | 4 | 0.5 | 0.25 | 16-32 | 16-32 | 32 | 256 |
| 37 | HB101/pAG21-1 | APH(3') | 4 | 0.25 | 0.125 | 1-2 | >256 | >256 | >256 |

[a]The full designation (No.) is AG01 etc. Only the last two digits are shown. All tested bacteria belong to the species *E. coli*
[b]clin. isol. = clinical isolate; RM = resistance mechanism

TABLE 3

| | Apramycin | | | Amikacin | | | Streptomycin | | |
|---|---|---|---|---|---|---|---|---|---|
| Strain no. | 0.25 | 1 | 4 | 0.25 | 1 | 4 | 0.25 | 1 | 4 |
| 176949/08 | R | S | S | R | S | S | S | S | S |
| 177581/08 | R | S | S | R | S | S | S | S | S |
| 177958/08 | R | S | S | R | S | S | R | S | S |
| 178122/08 | R | S | S | — | — | — | — | — | — |
| 178242/08 | R | S | S | — | — | — | — | — | — |
| 178331/08 | R | S | S | R | S | S | R | S | S |
| 178557/08 | R | S | S | R | S | S | R | S | S |
| 178594/08 | R | S | S | — | — | — | — | — | — |
| 177712/08 | R | S | S | — | — | — | — | — | — |
| 177809/08 | R | S | S | — | — | — | — | — | — |

Example 4

Apramycin Activity Against Clinical Isolates of Multidrug-Resistant *M. tuberculosis* (Table 4)

Activity of apramycin (μg/ml) was tested as in Example 3. R=resistant, S=susceptible.

TABLE 4

| | Apramycin | | | |
|---|---|---|---|---|
| Strain no. | 0.25 | 1 | 4 | 10 |
| 186005/09 | R | S | S | S |
| 186010/09 | R | S | S | S |
| 186013/09 | R | S | S | S |
| 186014/09 | R | S | S | S |
| 186002/10 | R | S | S | S |

Example 5

Apramycin Activity in Comparison to Amikacin Against Clinical Isolates of Non-Tuberculous Slow-Growing Mycobacteria (Table 5)

Activity of apramycin and amikacin (μg/ml) was tested as in Example 3.
R=resistant, S=susceptible.

TABLE 5

| | Apramycin | | | Amikacin | | |
|---|---|---|---|---|---|---|
| Strain no. | 1 | 4 | 10 | 1 | 4 | 10 |
| 182034/06 *M. avium-intracellulare* | R | S | S | R | S | S |
| 182124/07 *M. avium-intracellulare* | R | S | S | R | S | S |
| 182550/07 *M. avium-intracellulare* | R | S | S | R | S | S |
| 177227/06 *M. kansasii* | R | S | S | R | S | S |
| 180235/06 *M. kansasii* | R | S | S | R | S | S |

Example 6

Apramycin Activity (μg/ml) in Comparison to Commercially Available Aminoglycosides Against Clinical Isolates of Non-Tuberculous Rapidly-Growing Mycobacteria (Table 6)

Activity of apramycin was assessed in standard microdilution assays and is expressed as minimal inhibitory concentration (MIC) in μg/ml.

TABLE 6

| Strain no. | Apramycin | Amikacin | Kanamycin | Tobramycin |
|---|---|---|---|---|
| 500039/08 *M. abscessus* | 0.5 | 1.0 | 4.0 | 4.0 |
| 500044/09 *M. massiliense* | 2.0 | 1.0 | 16.0 | 8.0 |
| 177217/10 *M. massiliense* | 4.0 | 8.0 | 32.0 | 32.0 |
| 186139/07 *M. massiliense* | 4.0 | 4.0 | 32.0 | 16.0 |
| 181739/08 *M. bolletii* | 4.0 | 4.0 | 64.0 | 32.0 |
| 179639/10 *M. bolletii* | 4.0 | 8.0 | 64.0 | 32.0 |
| 183177/08 *M. bolletii* | 2.0 | 8.0 | 16.0 | 16.0 |

Example 7

Drug Selectivity Activity of Apramycin for Various Ribosomes in Comparison to Tobramycin, Gentamicin and Neomycin (Table 7)

A single rRNA allelic strain of *Mycobacteriumn smegmatis* was used for rRNA mutagenesis (Sander et al., Mol. Microbiol. 1996, 22:841-848). Key nucleotides which distinguish the prokaryotic from the eukaryotic decoding site are rRNA positions 1408 (bacterial ribosome: A, eukaryotic cytosolic ribosomes: G) and 1491 (bacterial ribosomes: G, eukaryotic cytosolic ribosomes: A, eukaryotic mitochondrial ribosomes).

Various versions of the eukaryotic drug binding site were transplanted into the bacterial ribosome (WO 2008/092690) to result in hybrid ribosomes, termed mitohybrid ribosomes, cytohybrid ribosomes, deafness 1555G ribosomes, deafness 1494U ribosomes (for methodology, rationale and hybrid ribosomes used, see Hobbie et al., Nucleic Acids Res. 2007, 35:6086-6093; Proc. Natl. Acad. Sci. USA 2008, 105:3244-3249; Proc. Natl. Acad. Sci. USA 2008, 105:20888-20893).

Ribosomal drug susceptibility was studied by measuring the minimal inhibitory concentrations, as described in Pfister et al., Animicrob. Agents Chemother. 2003, 47:1496-1502. The recombinants carrying the respective mutational alterations were subjected to determinations of minimal inhibitory concentrations (MIC) to assess ribosomal drug susceptibility. Cultures from single colonies were grown in LB medium supplemented with 0.05% Tween 80 and used for MIC tests in a microtiter plate format. Starting cultures contained 200 μl of bacterial cells at an optical density of 0.025 at 600 nm, and the respective drug was added in twofold series of dilution. The MIC was defined as the drug concentration at which the growth of the cultures was completely inhibited after 72 h of incubation at 25° C., corresponding to 24 generations.

Compared to tobramycin, gentamicin and neomycin, apramycin is more selective for bacterial ribosomes, as shown by the results in Table 7. This is demonstrated by the finding that apramycin has activity against wildtype bacterial ribosomes similar to that of tobramycin, gentamicin and neomycin, but much less activity against mutant ribosomes with the "humanized" drug binding sites. Hence, apramycin affects the mammal mitochondrial and cytosolic ribosome less than available 4,5- and 4,6-aminoglycosides.

TABLE 7

Activity of apramycin against recombinant ribosomes

|  | bacterial ribosomes | mitohybrid ribosomes | deafness 1555G ribosomes | deafness 1494U ribosombes | cytohybrid ribosomes |
|---|---|---|---|---|---|
| Apramycin | 1-2 | 1024 | 1024 | 1024 | >1024 |
| Tobramycin | 1 | 128 | 16 | 16 | 512 |
| Gentamicin | 1 | 128 | 16 | 16 | 1024 |
| Neomycin | 1 | 32 | 8 | 8 | 1024 |

Example 8

Cochleatoxicity In Vitro (Table 8)

Figure 1:
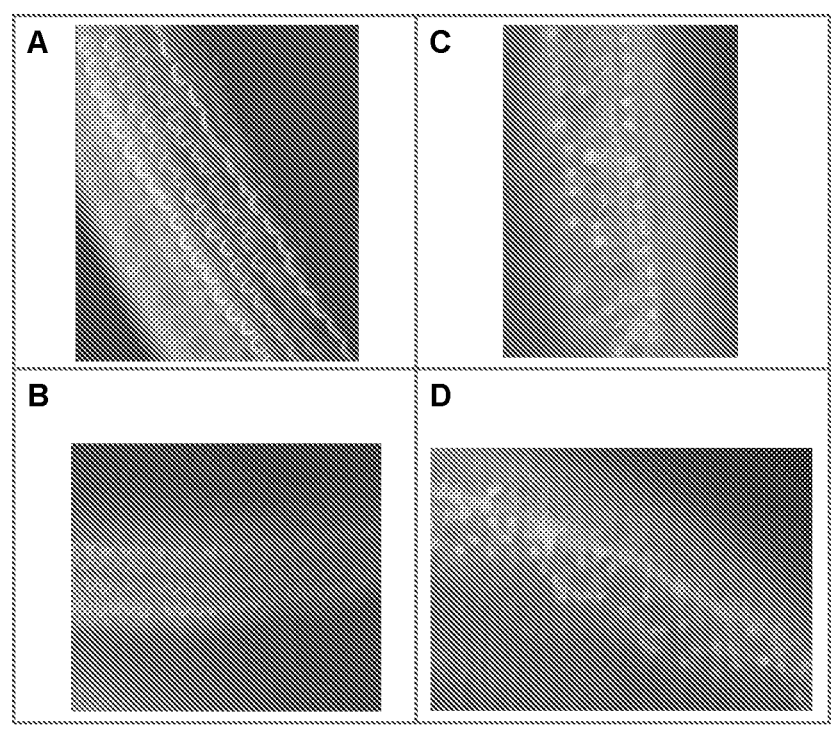
FIG. 1: Cochleatoxicity in vitro

Cochlear explants from newborn mice were treated with 0.5 mM aminoglycoside compound for 24 h; subsequently hair cell damage was assessed by epifluorescence microscopy. Results are shown in Table 8 and in FIG. 1.

TABLE 8

| Hair cell count | |
|---|---|
| Gentamicin | almost all hair cells (inner and outer) missing |
| Neomycin | |
| Apramycin | no hair cells missing (<5%) |
| Drug free control | no hair cells missing (<5%) |

Example 9

General Toxicity

Guinea pigs received a systemic application of aminoglycosides once daily in the dosing indicated in Table 9 for 14 days and were then monitored for an additional 14 days. Results are shown in Table 9.

TABLE 9

| Drug | mg/kg base | mg/kg gentamicin base equivalent | number of animals | observations |
|---|---|---|---|---|
| Gentamicin | 120 | 120 | 6 | normal weight gain |
|  | 140 | 140 | 8 | significant weight loss |
|  | 160 | 160 | 3 | 2 out of 3 died |
| Apramycin | 152 | 132 | 2 | normal weight gain |
|  | 184 | 160 | 1 | normal weight gain |
|  | 217 | 188 | 5 | normal weight gain |
|  | 355 | 309 | 2 | less weight gain |
|  | 432 | 376 | 5 | less weight gain |
|  | 649 | 564 | 5 | less weight gain |

For one animal each with a dose of 432 and 649 mg/kg apramycin, necropsy was done at the end of the experiment. The animals showed good general condition; no significant lesions or gross findings were observed for the integumentary system, respiratory system, cardiovascular system, urogenital system, endocrine system, nervous system, lymphatic system, musculoskeletal system and gastrointestinal system.

Kidney Histopathology, 432 mg/kg Apramycin:

Description: few, small lymphoplasmacytic aggregates in the renal interstitium. These changes affect less than 5% of the renal mass in the sections.

Interpretation: Mild, multifocal interstitial lymphoplasmacytic inflammation.

Comments: The degree of inflammation within the interstitium is minimal and is considered a background incidental finding for the species. Tubular necrosis or other evidence of nephrotoxicity is not histologically evident.

Kidney Histopathology, 649 mg/kg Apramycin:

Description: few, small foci of tubular degeneration and regeneration in the superficial cortex. These changes affect less than 5% of the renal mass in the sections.

Interpretation: Mild, multifocal tubular nephrosis.

Comments: The foci of tubular nephrosis are minimal in these sections and appear unlikely to significantly impact renal function.

Example 10

Cochleatoxicity In Vivo as Determined by Auditory Brain Stem Response (ABR) (FIG. 2b)

Guinea pigs received a systemic application of aminoglycosides once daily in the dosing indicated for 14 days, and were allowed to rest for 14 days before post-treatment ABR was taken. Results are shown in FIG. 2b.

Example 11

Synthesis of Apramycin Derivatives

The following compounds were synthesized based on standard procedures:

ETH 99: Compound of formula (II), wherein $R^9R^{10}$ is C=O, $R^{13}$ is γ-amino-α-hydroxybutyryl, $R^{16}$ is methyl, and all other substituents are hydrogen, tetraacetate salt;

ETH 100: Compound of formula (II), wherein $R^7$ is γ-amino-α-hydroxybutyryl, $R^{16}$ is methyl, and all other substituents are hydrogen, teatraacetate salt;

ETH 101: Compound of formula (II), wherein $R^3$ and $R^7$ are γ-amino-α-hydroxybutyryl, $R^{16}$ is methyl, and all other substituents are hydrogen, teatraacetate salt;

ETH 102: Compound of formula (II), wherein $R^1$ is γ-amino-α-hydroxybutyryl, $R^{16}$ is methyl, and all other substituents are hydrogen, tetraacetate salt;

ETH 103: Compound of formula (II), wherein $R^7$ is γ-phthaloylamino-α-hydroxybutyryl, $R^{16}$ is methyl, and all other substituents are hydrogen, teatraacetate salt;

ETH 105: Compound of formula (II), wherein $R^{13}$ is γ-amino-α-hydroxybutyryl, $R^{16}$ is methyl, and all other substituents are hydrogen, teatraacetate salt.

Scheme 1

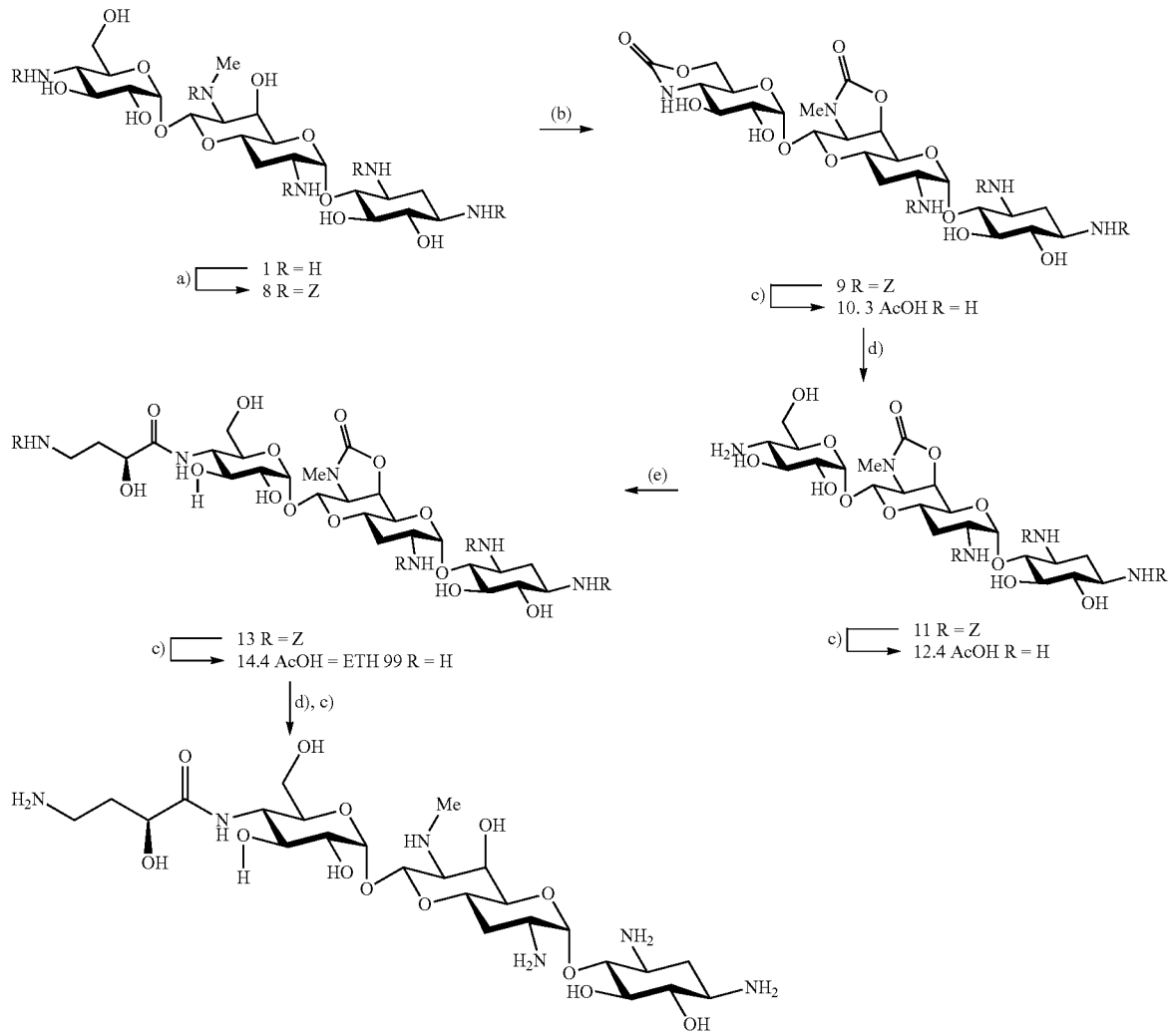

15 = ETH 105

Reagents and conditions: a) ZCl, Na₂CO₃, MeOH/H₂O; 74%. b) NaH, DMF; 68%.
c) Pd(OH)₂/C, H₂ (1 atm), dioxane/AcOH/H₂O 4:4:1; 95% of 10•3 AcOH; 90% of 12•4
AcOH; 85% of 14•4 AcOH = ETH 99 and 12% of 15 = ETH 105 (from 13). d) Ba(OH)₂.
H₂O, dioxane/H₂O 2:1; 70% of 11. e) (benzyloxy-(S)-4-carbonylamino)-2-hydroxybutanoic
acid, N-hydroxysuccinimide, DCC, Et₃N, THF; 85%.

1,3,2',7',4"-Pentakis-N-(benzyloxycarbonyl)apramycin (8)

Benzyloxycarbonyl chloride (26.9 g, 157 mmol) was added dropwise to a vigorously stirred mixture of apramycin (1; 10 g, 18.5 mmol) and Na₂CO₃ (29.5 g, 278 mmol) in 3:7 H₂O/MeOH (240 ml) at 0° C. The mixture was stirred for 30 min at 0° C., and for 20 h at 26° C. After addition of MeOH (200 ml) the inorganic precipitate was removed by filtration, and the filtrate was evaporated. The residue was triturated with H₂O. The aq. phase was discarded. The organic phase was dissolved in MeOH/AcOEt and pre-adsorbed on silica-gel. FC (AcOEt/CHCl₃/MeOH 4:4:0→4:4:1) gave 8 (8.95 g, 74%). White solid. Rf (CHCl₃/AcOEt/MeOH 4:4:1) 0.35. IR (ATR): 3388w, 3331w, 2944w, 1692s, 1520m, 1454m, 1405m, 1306m, 1246m, 1141m, 1074m, 1016s, 996s, 772m, 735m, 695s. $[\alpha]_D^{25}$=+68.7 (c=1.0, MeOH). ¹H-NMR (600 MHz, CD₃OD): 7.44-7.19 (m, 25H arom.); 5.34-5.24 (m, H—C(1'), H—C(8'), H—C(1")); 5.17-4.97, 4.18-4.09, 3.89-3.73, 3.70-3.37, 3.24-3.18 (several m, H—C(1), H—C(3), (H—C(4), H—C(5), H—C(6), H—C(2'), H—C(4'), H—C(5'), H—C(6'), H—C(7'), H—C(8'), H—C(2"), H—C(3"), H—C(4"), H—C(5"), H—C(6"), 5CH₂Ph); 3.11 (s, NMe); 2.09-2.03 (m, $H_{eq}$—C(2), $H_{eq}$—C(3)); 1.77 (q, J=11.8, $H_{ax}$—C(3')); 1.46 (q, J=12.5, $H_{ax}$—C(2)). ¹³C-NMR (150 MHz, CD3OD): 159.77, 159.11, 158.68, 158.67, 158.20 (5 s, 5C=O); 138.36, 138.31, 138.27, 138.05, 138.02 (5 s arom.); 129.52-128.89 (several d arom.); 101.15 (d, C(1')); 99.60 (d, C(1")); 98.50 (d, C(8')); 96.29, 95.75 (2 d); 92.30 (d); 85.30, 82.78, 78.62, 76.64, 76.34 (5 d); 74.10, 74.04, 73.78, 71.87, 71.66, 71.48 (6 d); 68.71, 67.78, 67.69, 67.66, 67.56 (5 t, 5PhCH₂); 68.09, 67.98 (2 d); 66.69 (d); 63.19 (t, (6")); 62.83, 60.97 (2 d); 55.51, 54.78, 52.91, 52.15, 51.88, 51.71, 51.45 (7 d); 33.39, 31.40 (2 t, C(2), C(3')); 30.11 (q, NMe). HR-MALDI-MS: 1232.4540 (100, [M+Na]$^+$, $C_{61}H_{71}N_5NaO_{21}^+$; calc. 1232.4539).

1,3,2'-Tris-N-(benzyloxycarbonyl)-7'-N,6'-O-carbonyl-4''-N-6''-O-carbonyl-apramycin (9)

A solution of 8 (3.123 g, 2.58 mmol) in anhydrous DMF (20 ml) was treated with NaH (198 mg, 5.16 mmol, 60% dispersion in mineral oil) at 0°. The reaction mixture was allowed to warm to 26° C. within 2 h, and stirred for further 2 h at 26° C. The mixture was quenched with 1N aq. AcOH (5 ml) and evaporated to dryness. The syrup obtained was dissolved in MeOH/AcOEt and pre-adsorbed on silicagel. FC (AcOEt/CHCl$_3$/MeOH 4:4:0→4:4:1) gave 9 (1.75 g, 68%), white solid. Rf (CHCl$_3$/AcOEt/MeOH 4:4:1) 0.20. IR (ATR): 3317w (br.), 2937w, 1750 (sh.), 1704s, 1697s, 1525m, 1454m, 1410m, 1339m, 1256m, 1139m, 1075s, 1027s, 1002s, 980s, 757m, 739s, 697s. $[\alpha]_D^{25}$=+64.6 (c=1.0, MeOH/45 μl DMSO). $^1$H-NMR (600 MHz, Pyr-d$_5$): 9.49 (s, HN—C(4'')); 8.35 (s, HN—C(1), HN—C(3)); 7.79 (s, HN—C(2')); 7.45-7.26 (m, 15H arom.); 5.83-5.63 (m, H—C (1'), H—C(1'')); 5.40-5.06 (m, H—C(6'), H—C(8'), 3CH$_2$Ph); 5.00 (br. s, 4OH); 4.50-4.46 (H—C(4''), H$_{eq}$—C (6'')); 4.33 (t, J=10.3, H$_{ax}$—C(6'')); 4.24-4.12 (m, H—C(4), H—C(2'), H—C(2''), H—C(5'')); 4.02-3.97 (m, H—C(1), H—C(5)); 3.87-3.78 (m, H—C(3), H—C(4'), H—C(5')); 3.68 (t, J=9.7, H—C(3'')); 3.43 (br. d, J=9.0, H—C(7')); 2.87 (s, NMe); 2.61-2.58 (m, H$_{eq}$—C(3')); 2.39-2.37 (m, H$_{eq}$—C (2)); 2.31 (q, J=11.6, H$_{ax}$—C(3')); 2.23-2.19 (m, H$_{ax}$—C(2)). $^{13}$C-NMR (150 MHz, Pyr-d$_5$): 157.91, 157.19, 156.70, 156.46, 153.19 (5 s, 5C=O); 138.14, 137.95, 137.34 (3 s arom.); 128.99-128.14 (several d arom.); 100.29 (d, C(1')); 96.04 (d, C(1'')); 91.07 (d, C(8')); 84.03 (d, C(4)); 78.16, 76.31, 73.11 (3 d, C(4'), C(5'), C(2'')); 71.83 (d, C(4'')); 70.31 (d, C(6')); 68.37 (t, C(6'')); 66.69, 66.27, 66.29 (3 t, 3PhCH$_2$); 66.21 (d, C(5)); 65.81 (d, C(6)); 63.88 (d, C(5'')); 59.65 (d, (7')); 58.13 (d, C(3'')); 52.82 (d, C(1)); 51.79 (d, C(3)); 51.39 (d, C(2')); 35.23, 32.49 (2 t, C(2), C(3')); 29.66 (q, NMe). HR-MALDI-MS: 1016.3383 (100, [M+Na]$^+$, $C_{47}H_{55}N_5NaO_{19}^+$; calc. 1016.3389).

7'-N,6'-O-Carbonyl-4''-N,6''-O-carbonyl-apramycin triacetate (10)

A solution of 9 (30 mg, 30 μmol) in 80% aq. AcOH (1.0 ml) and dioxane (0.8 ml) was treated with 20% Pd(OH)$_2$/C (30 mg) and stirred under H$_2$ (1 atm) for 15 h. The mixture was filtered through Celite, washing with H$_2$O, and the filtrate was evaporated. A solution. of the residue in H$_2$O was washed with CH$_2$Cl$_2$. Lyophilisation of the aq. solution gave 10·3AcOH (22 mg, 95%). Light brown solid. IR (ATR): 3349w (br.), 3222w (br.), 2924w, 1747m, 1707m, 1552s, 1407s, 1147m (sh), 1098m (sh), 1078m (sh), 1026s (sh), 980s, 760m. $^1$H-NMR (500 MHz, D$_2$O): 5.63 (d, J=3.4, H—C (1')); 5.35 (d, J=3.8, H—C(1'')); 5.24 (d, J=1.7, H—C(8')); 5.06 (dd, J=9.4, 3.2, H—C(6')); 4.67 (embedded in HOD signal), H—C(5')); 4.30 (dd, J=9.8, 4.9, H$_{eq}$—C(6'')); 4.20 (dd, J=9.4, 1.7, H—C(7')); 4.13 (t, J=10.4, H$_{ax}$—C(6'')); 3.98 (td, J=10.1, 4.8, H—C(5'')); 3.88 (td, J=10.9, 4.0, H—C(4')); 3.82 (t, J=9.7, H—C(4)); 3.70 (dd, J=9.5, 4.0, H—C(2'')); 3.64-3.60 (m, H—C(3''); 3.54 (m, H—C(5), H—C(2')); 3.47 (t, J=9.7, H—C(6)); 3.40-3.34 (m, H—C(3)); 3.27-3.19 (m, H—C(1), H—C(4'')); 2.82 (s, NMe); 2.40 (dt, J=12.8, 4.0, H$_{eq}$—C(2)), 2.28 (dt, J=10.9, 4.3, H$_{eq}$—C(3)); 1.98 (q, J=12.0, H$_{ax}$—C(3)), 1.82 (br. s, 3MeCO$_2$); 1.73 (q, J=12.9, H$_{ax}$—C(2)). $^{13}$C-NMR (125 MHz, D$_2$O): 180.17 (s, 4OC=O); 159.02 (s, MeNC=O); 155.21 (s, HNC=O); 95.56 (d, C(1')); 94.56 (d, C(1'')); 90.18 (d, C(8')); 78.27 (d, C(4)); 74.97 (d, C(5)); 72.35 (d, C(6)); 70.52 (d, C(2'')); 69.63 (d, C(3'')); 69.20 (d, C(6')); 67.62 (t, C(6'')); 65.11 (d, C(5')); 64.03 (d, C(4')); 61.99 (d, C(5'')); 58.87 (d, C(7')); 55.52 (d, C(4'')); 49.58 (d, C(1)); 48.42 (d, C(3)); 47.71 (d, C(2')); 29.08 (q, NMe); 28.51, 28.39 (2t, C(2), C(3')); 22.81 (q, 3MeC=O). HR-MALDI-MS: 566.2670 (100, [M+H]$^+$, $C_{22}H_{40}N_5O_{12}^+$; calc. 566.2673).

1,3,2'-Tris-N-(benzyloxycarbonyl)-7'-N,6'-O-carbonyl-apramycin (11)

A solution of 9 (0.2 g, 0.2 mmol) in 2:1 dioxane/H$_2$O (15 ml) was treated with Ba(OH)$_2$.H$_2$O (76 mg, 0.4 mmol) and stirred at 70° C. for 3 h. After cooling to room temperature, the mixture was neutralized with CO$_2$, and evaporated. H$_2$O was removed by co-evaporation with toluene. The residue was taken in MeOH and filtered through Celite. The combined filtrate and washings were evaporated. FC(CHCl$_3$/MeOH/aq. NH$_3$ (25%) 80:20:0→80:15:5) gave 11 (136 mg, 70%), white solid. Rf (CHCl$_3$/MeOH/aq. NH$_3$ (25%) 70:15:2) 0.20. IR (ATR): 3306w (br.), 2937w, 1744m (sh.), 1690s, 1530m, 1455m, 1392m, 1302m (sh.), 1255m, 1224m, 1131m, 1070m (sh.), 1032s, 1000s, 852m, 736m, 696s. $[\alpha]_D^{25}$=+64.7 (c=0.5, MeOH). $^1$H-NMR (600 MHz, Pyr-d$_5$): 8.56 (d, J=8.1, HN—C(1)); 8.41 (d, J=8.4, HN—C(3)); 8.00 (d, J=7.3, HN—C(2')); 7.46-7.22 (m, 15H arom.); 5.80-5.76 (m, H—C (1'), H—C(1'')); 5.47-5.01 (m, H—C(6'), H—C(7'), H—C (8'), 3CH$_2$Ph, NH$_2$, 5OH); 4.44 (t, J=9.2, H—C(5'')); 4.38 (dd, J=11.7, 2.6, H—C(6'')); 4.23-4.17, 4.07-4.04, 4.00-3.84 (several m, H—C(1), H—C(3), H—C(4), H—C(5), H—C (6), H—C(2'), H—C(4'), H—C(1''), H—C(2''), H—C(3'')); 3.43 (dd, J=8.8, 2.3, H—C(5')); 3.34 (t, J=9.6, H—C(4'')); 2.87 (s, NMe); 2.55-2.52 (m, H$_{eq}$—C(3')); 2.45-2.41 (m, H$_{eq}$—C(2)); 2.34 (q, J=11.7, H$_{ax}$—C(3')); 2.22 (q, J=12.7, H$_{ax}$—C(3)). $^{13}$C-NMR (150 MHz, Pyr-d$_5$): 157.87, 157.22, 156.76, 156.59 (4 s, 4C=O); 138.15, 137.98, 137.49 (3 s arom.); 129.03-128.16 (several d arom.); 100.16 (d, C(1')); 95.29 (d, C(1'')); 91.00 (d, C(8')); 83.73 (d); 78.24, 76.34, 76.04, 74.67, 73.37, 70.74 (6 d); 66.72, 66.30, 66.25, (3 t, 3PhCH$_2$); 66.35, 65.84 (d); 63.30 (t, C(6'')); 59.65 (d); 55.72 (d); 52.81, 51.79, 51.31 (3 d); 35.50, 32.73 (2 t, C(2), C(3')); 29.77 (q, NMe). HR-MALDI-MS: 990.3590 (100, [M+Na]$^+$, $C_{46}H_{57}N_5NaO_{18}^+$; calc. 990.3590).

7'-N,6'-O-Carbonyl-apramycin tetraacetate (12)

A solution of 11 (30 mg, 31 μmol) in 80% aq. AcOH (1.0 ml) and dioxane (0.8 ml) was treated with 20% Pd(OH)$_2$/C (30 mg) and stirred under H$_2$ (1 atm) for 15 h. The mixture was filtered through Celite, washing with H$_2$O. The combined filtrate and washings were evaporated. A solution of the residue in H$_2$O was washed with CH$_2$Cl$_2$. Lyophilisation of the aq. solution gave 12·4AcOH (22.5 mg, 90%), light brown solid. IR (ATR): 3321w (br.), 3162w (br.), 2928w, 1742m, 1539s, 1403s, 1338m, 1030m (sh), 988s, 925m, 759m. $^1$H-NMR (500 MHz, D$_2$O): 5.64 (br. s, H—C(1')); 5.39 (d, J=3.4, H—C(1'')); 5.28 (br. s, H—C(8')); 5.09 (dd, J=9.3, 3.3, H—C(6')); 4.76 (embedded in HOD signal), H—C(5')); 4.24 (dd, J=9.3, 1.5, H—C(7')); 3.97-3.88 (m, H—C(4'), H—C (3'')); 3.82-3.69 (m, H—C(4), H—C(2''), H—C(5''), 2H—C (6'')); 3.60-3.56 (m, H—C(5), H—C(2')); 3.51 (t, J=9.7, H—C(6)); 3.35-3.29 (m, H—C(3)); 3.26 (td, J=14.1, 6.9, H—C(1)); 3.20 (t, J=10.0, H—C(4'')); 2.88 (s, NMe); 2.41-2.39 (m, H$_{eq}$—C(2)), 2.36-2.33 (m, H$_{eq}$—C(3)); 2.03 (q, J=12.0, H$_{ax}$—C(3')), 1.88 (br. s, 4MeCO$_2$); 1.73 (q, J=12.9, $H_{ax}$—C(2)). $^{13}$C-NMR (125 MHz, $D_2O$): 181.07 (s, 4OC=O); 159.16 (s, MeNC=O); 95.84 (d, C(1')); 93.57 (d, C(1")); 90.46 (d, C(8')); 79.45 (d, C(4)); 75.18 (d, C(5)); 72.63 (d, C(6)); 70.52 (d, C(2")); 69.63, 69.20 (2 d, C(6'), C(3")); 65.52 (d, C(5')); 64.24 (d, C(4')); 62.41 (d, C(5")); 60.16 (t, C(6")); 59.08 (d, C(7')); 52.17 (d, C(4")); 49.84 (d, C(1)); 48.50 (d, C(3)); 47.88 (d, C(2')); 29.25 (q, NMe); 28.56, 28.26 (2t, C(2), C(3')); 22.99 (q, 4MeC=O). HR-MALDI-MS: 588.2495 (27, [M+Na]$^+$, $C_{22}H_{39}N_5NaO_{12}^+$; calc. 588.2493), 566.2673 (52, [M+H]$^+$, $C_{22}H_{40}N_5O_{12}$; calc. 566.2673).

1,3,2'-Tris-N-(benzyloxycarbonyl)-7'-N,6'-O-carbonyl-4"-N-[(2S)-4-amino-2-hydroxy-butyryl]apramycin (13)

A mixture of (benzyloxy-(S)-4-carbonylamino)-2-hydroxybutanoic acid (19 mg, 75 μmol), N-hydroxysuccinimide (8.6 mg, 75 μmol), and DCC (15.4 mg, 75 μmol) in anhydrous THF (2 ml) was stirred at 26° C. for 2.0 h. The mixture was treated with a solution of 11 (60 mg, 62 μmol) and triethylamine (17 μl, 122 μmol) in dry THF (3 ml), and stirred for 20 h. Evaporation gave a white solid that was dissolved in $CH_2Cl_2$/MeOH and pre-absorbed on silica gel. FC($CHCl_3$/MeOH/aq. $NH_3$ (25%) 90:10:0→90:10:1) gave 13 (63 mg, 85%), white solid. $R_f$($CHCl_3$/MeOH/aq. $NH_3$ (25%) 75:15:2) 0.39. IR (ATR): 3330m (br.), 2936w, 1748w (sh), 1696s, 1527s, 1454w, 1407w, 1263m, 1141m, 1033s, 1002s, 738m, 697m. $[\alpha]_D^{25}$=+52.6 (c=0.5, MeOH). $^1$H-NMR (500 MHz, $CD_3OD$): 7.44-7.25 (m, 20H arom.); 5.23 (d, J=3.8, H—C(1')); 5.14 (br. s, H—C(8'), H—C(1")); 5.09-5.00 (m, 4$CH_2$Ph); 4.99 (br. d, J=7.8, H—C(6')); 4.66 (dd, J=9.3, 2.1, H—C(7')); 4.58 (dd, J=10.5, 2.7, CH(OH)$CH_2CH_2$); 4.12 (m, H—C(4')); 3.95 (t, J=9.5, H—C(4)); 3.70-3.43 (m, H—C(5), H—C(6), H—C(2'), H—C(5'), H—C(2"), H—C(3"), H—C(4"), H—C(5"), 2H—C(6")); 3.33-3.20 (m, H—C(1), H—C(3), CH(OH)$CH_2CH_2$); 2.78 (s, NMe); 2.15-2.07 (m, $H_{eq}$—C(2), $H_{eq}$—C(3)); 2.01-1.85 (m, CH(OH)$CH_2CH_2$), $H_{ax}$—C(3')); 1.55 (q, J=12.1, $H_{ax}$—C(2)). $^{13}$C-NMR (125 MHz, CD3OD): 177.67 (s, NC=O); 159.79 (s, MeNC=O); 159.03, 158.70, 158.13, 158.05 (5 s); 138.44, 138.38, 138.26, 138.03 (4 s arom.); 129.79-128.83 (several d arom.); 101.12 (d, C(1')); 96.18 (d, C(1")); 92.46 (d, C(8')); 85.20 (d, C(6)); 78.11 (d); 76.31 (d); 73.87 (d); 73.71 (d); 71.58 (d); 70.94, 67.92, 67.63, 67.44 (4 t, 4Ph$CH_2$); 66.65 (t, (6")); 63.14 (d); 60.88 (d); 53.48 (d); 52.74 (d); 52.19 (d); 51.88 (d); 38.12 (t); 35.81 (t); 35.39 (t); 33.00 (t); 30.03 (q, NMe). HR-MALDI-MS: 1225.4458 (100, [M+Na]$^+$, $C_{58}H_{70}N_6NaO_{22}^+$; calc. 1225.4435).

7'-N,6'-O-Carbonyl-4"-N-[(2S)-4-amino-2-hydroxy-butyryl]apramycin tetraacetate (14=ETH 99)

A solution of 13 (25 mg, 21 μmol) in 80% aq. AcOH (1.0 ml) and dioxane (0.8 ml) was treated with 20% Pd(OH)$_2$/C (25 mg) and stirred under $H_2$ (1 atm) for 15 h. The mixture was filtered through Celite, washing with $H_2O$. The combined filtrate and washings were evaporated. A solution of the residue in $H_2O$ was washed with $CH_2Cl_2$. Lyophilisation of the aq. solution gave 14=ETH 99 (16 mg, 85%), light brown solid. IR (ATR): 3170w (br.), 2936w, 1747w, 1548s, 1403s, 1339m, 1038m (sh), 992s, 759m. $^1$H-NMR (500 MHz, $D_2O$): 5.69 (d, J=3.6, H—C(1')); 5.41 (d, J=3.8, H—C(1")); 5.33 (d, J=2.1, H—C(8')); 5.16 (dd, J=9.3, 3.4, H—C(6')); 4.80 (embedded in HOD signal), H—C(5')); 4.35 (dd, J=8.2, 4.0, CH(OH)$CH_2$); 4.29 (dd, J=9.3, 2.1, H—C(7')); 3.99 (td, J=11.0, 4.1, H—C(4')); 3.90-3.74 (m, H—C(4), H—C(2"), H—C(3"), H—C(4"), H—C(5")); 3.68-3.54 (m, H—C(5), H—C(6), H—C(2'), 2H—C(6")); 3.32-3.26 (m, H—C(1), H—C(3)); 3.21-3.14 (m, CH(OH)$CH_2CH_2$); 2.94 (s, NMe); 2.43-2.38 (m, $H_{eq}$—C(2), $H_{eq}$—C(3)); 2.22-2.16 (m, CH(OH)$CH_2_a$); 2.11 (q, J=12.1, $H_{ax}$—C(3')), 2.06-2.00 (m, CH(OH)$CH_2_b$); 1.88 (br. s, 4MeCO$_2$); 1.76 (q, J=12.1, $H_{ax}$—C(2)). $^{13}$C-NMR (125 MHz, $D_2O$): 180.17 (s, 4OC=O); 175.83 (s, NC=O); 159.03 (s, MeNC=O); 95.67 (d, C(1')); 93.57 (d, C(1")); 90.12 (d, C(8')); 80.15 (d, C(4)); 75.13 (d, C(5)); 72.67 (d, C(6)); 71.29 (d, C(2")); 70.73 (d, C(3")); 69.44, 69.33, 69.30 (3 d, $CH_2CH(OH)CO$, C(6'), C(5")); 65.12, 64.12 (2 d, C(4'), C(5')); 60.46 (t, C(6")); 59.02 (d, C(7')); 51.11 (d, C(4")); 49.85 (d, C(1)); 48.40 (d, C(3)); 47.82 (d, C(2')); 36.34 (t, CH(OH)$CH_2CH_2$); 30.68 (t, CH(OH)$CH_2CH_2$); 29.85 (d, C(2)); 29.10 (q, NMe); 28.65 (t, C(3')); 22.98 (q, 4MeC=O). HR-MALDI-MS (negative mode): 665.3001 (100, [M–H]$^-$, $C_{26}H_{45}N_6O_{14}^-$; calc. 665.2994).

4"-N-[(2S)-4-Amino-2-hydroxybutyryl]apramycin (15=ETH 105)

A solution of 13 (50 mg, 41.6 μmol) in 2:1 dioxane/$H_2O$ (9 ml) was treated with Ba(OH)$_2$.$H_2O$ (15.7 mg, 83 μmol) and stirred at 50° C. for 6 h. After cooling to room temperature the mixture was neutralized with $CO_2$, and evaporated ($H_2O$ was removed by co-evaporation with toluene). The residue was taken in MeOH and filtered through Celite. The combined filtrate and washings were evaporated. The residue was filtered through a short pad of silica gel ($CHCl_3$/MeOH/aq. $NH_3$ (25%) 80:20:0→80:15:1). The fractions eluted with $CHCl_3$/MeOH/aq. $NH_3$ (25%) 80:15:1 (MALDI-MS: 1196.5) were collected and evaporated. A solution of the residue (5.0 mg) in 80% aq. AcOH (1.0 ml) was treated with 20% Pd(OH)$_2$/C (5 mg) and stirred under $H_2$ (1 atm) for 15 h. The mixture was filtered through Celite, washing with $H_2O$. The combined filtrate and washings were evaporated. A solution of the residue in $H_2O$ was washed with $CH_2Cl_2$. Lyophilisation and FC (MeOH/aq. $NH_3$ (25%) 7:3) gave 15=ETH 105 (3.2 mg, 12%), white solid. IR (ATR): 3284w (br.), 2928w, 1637m, 1573m, 1455m, 1387m, 1336m, 1086s 1028s, 993s, 834m. $^1$H-NMR (600 MHz, $D_2O$): 5.37 (d, J=3.7, H—C(1')); 5.05 (d, J=3.6, H—C(1")); 4.85 (d, J=9.0, H—C(8')); 4.33-4.26 (m, H—C(6'), CH(OH)$CH_2CH_2$); 3.90-3.45 (several m, H—C(2'), H—C(5'), H—C(2"), H—C(3"), H—C(4"), H—C(5"), 2H—C(6")); 3.47 (td, J=9.0, 3.7, H—C(5)); 3.29 (t, J=9.0, H—C(6)); 3.17-2.97 (m, H—C(4), H—C(4'), CH(OH)$CH_2CH_2$); 2.88-2.84 (m, H—C(1)); 2.80-2.72 (m, H—C(3)); 2.70 (dd, J=8.8, 2.8, H—C(7')); 2.34 (s, NMe); 2.12-2.06 (m, $H_{eq}$C(3), CH(OH)$CH_a$$CH_2$); 2.02-1.90 (m, $H_{eq}$—C(2), CH(OH)$CH_b$$CH_2$); 1.72-1.63 (m, $H_{ax}$—C(3); 1.26-1.19 (m, $H_{ax}$—C(2). HR-MALDI-MS: 663.3178 (39, [M+Na]$^+$, $C_{25}H_{48}N_6NaO_{13}^+$; calc. 663.3177), 641.3359 (100, [M+H]$^+$, $C_{25}H_{49}N_6O_{13}^+$; calc. 641.3358).

Scheme 2

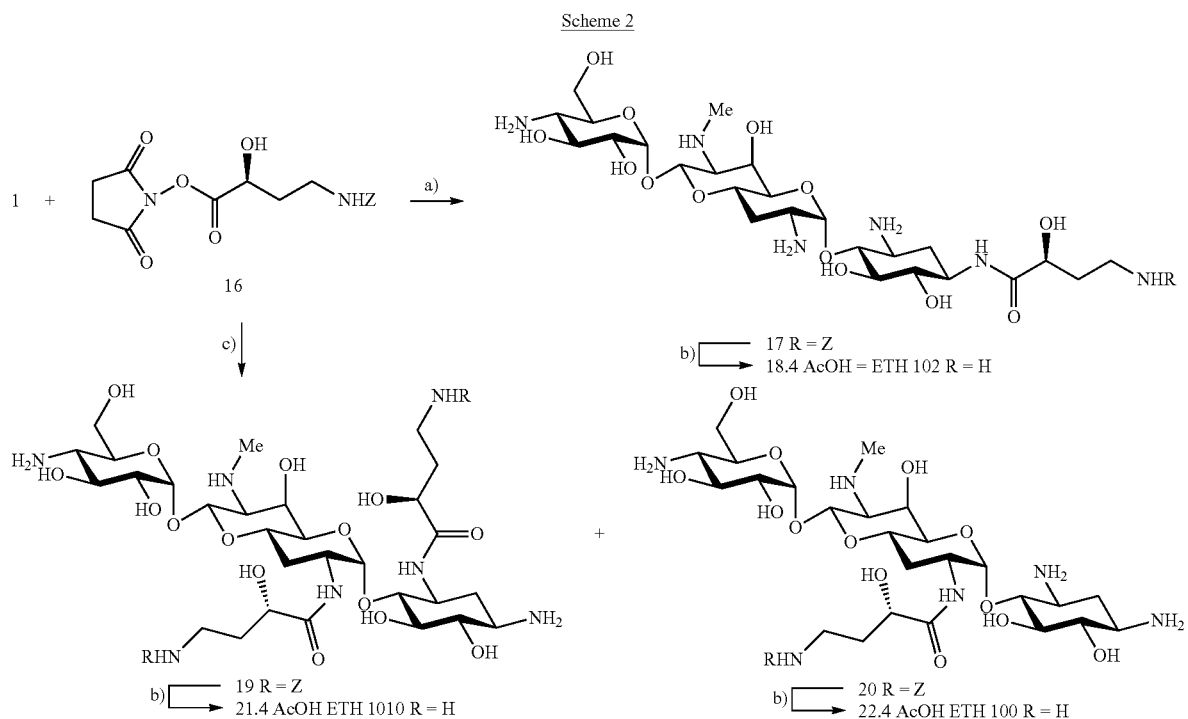

Reagents and conditions: a) Zn(OAc)₂•2 H₂O, DMF/H₂O; 42%. b) Pd(OH)₂/C, H₂ 1 atm), dioxane/AcOH/H₂O 4:4:1; 90% of 18•4 AcOH = ETH 102; 80% of 21•4 AcOH = ETH 101; 90% of 22•4 AcOH = ETH 100. c) Ni(OAc)₂. 4 H₂O, DMF/H₂O; 10% of 19 and 45% of 20.

1-N-[(2S)-4-(Benzyloxycarbonylamino)-2-hydroxybutyryl]apramycin (17)

A solution of 1 (400 mg, 0.74 mmol) in 1:5 H₂O/DMF (30 ml) was treated with zinc(II) acetate dehydrate (652 mg, 2.97 mmol, see Kirst et al., *Tet. Lett.* 1981, 22:295; Allen et al., *J. Med. Chem.* 1987, 30:333) and stirred for 1 h. The mixture was treated with N-[(2S)-4-(benzyloxycarbonylamino)-2-hydroxybutyryl]succinimide, DE 2555405) (16; 372 mg, 1.1 mmol) and stirred for 15 h at 26° C. After evaporation of the solvents, the residue was dissolved in CHCl₃/MeOH/aq. NH₃ (25%) 3:3:1 and pre-adsorbed on silicagel. FC (CHCl₃/MeOH/aq. NH₃ (25%) 10:10:1→3:3:1→0:4:1) and lyophilisation gave 17 (240 mg, 42%), white fluffy solid. $R_f$(MeOH/25% aq. NH₃ 4:1) 0.29. IR (ATR): 33280w (br.), 2944w, 1692w 1644w, 1531m, 1454w, 1407w, 1337w, 1265w, 1058s, 1033s, 1000s, 858m, 735m, 695s. ¹H-NMR (500 MHz, D₂O): 7.48-7.40 (m, 5H arom.); 5.69 (d, J=3.7, H—C(1')); 5.51 (d, J=3.9, H—C(1")); 5.21 (d, J=8.5, H—C(8')); 5.13 (br. s, PhCH₂); 4.59 (t, J=2.7, H—C(6')); 4.21 (dd, J=8.4, 3.8, CH(OH)CH₂CH₂); 4.01-3.93 (m, H—C(4'), H—C(3"), H—C(5")); 3.90-3.86 (m, H—C(3)); 3.84-3.79 (m, H—C(6), H—C(5'), H—C(6")); 3.72-3.62 (m, H—C(5), H—C(2'), H—C(2")); 3.55 (t, J=12.0, H—C(4)); 3.41-3.38 (m, H—C(1)); 3.36 (dd, J=8.5, 2.8, H—C(7')); 3.32-3.27 (m, CH(OH)CH₂CH₂); 3.13 (t, J=10.2, H—C(4")); 2.81 (s, NMe); 2.40 (dt, J=7.8, 3.3, $H_{eq}$—C(3')); 2.23 (dt, J=13.0, 4.1, $H_{eq}$—C(2)); 2.05 (q, J=11.6, $H_{ax}$—C(3')); 2.03-1.97 (m, CH(OH)CH$_a$CH₂); 1.88-1.78 (m, CH(OH)CH$_b$CH₂); 1.71 (q, J=12.7, $H_{ax}$—C(2)). ¹³C-NMR (125 MHz, D₂O): 176.24 (s, C=O); 158.15 (s, C=O); 136.29 (s, arom.); 128.57-127.44 (several d, arom.); 95.74 (d, C(1')); 94.37 (d, C(1")); 92.94 (d, C(8')); 75.61 (d, C(5)); 73.56 (d, C(4)); 70.27-69.01 (several d, C(6), C(4'), C(5'), C(2"), C(5"), CH(OH)CH₂CH₂); 66.64 (t, PhCH₂); 65.94 (d, C(3")); 62.78 (d, C(6')); 60.30 (t, C(6")); 59.38 (d, C(7')); 51.92 (d, C(4")); 48.76 (d, C(1)); 48.60 (d, C(3)); 47.91 (d, C(2)); 36.35 (t, CH(OH)CH₂CH₂); 33.25 (t, CH(OH)CH₂CH₂); 30.88 (t, C(2)); 30.06 (q, NMe); 30.27 (t, C(3')). HR-MALDI-MS: 797.3538 (63, [M+Na]⁺, C₃₃H₅₄N₆NaO₁₅⁺; calc. 797.3545), 775.3707 (100, [M+H]⁺, C₃₃H₅₅N₆O₁₅⁺; calc. 775.3725).

1-N-[(2S)-4-Amino-2-hydroxybutyryl]apramycin tetraacetate (18=ETH 102)

A solution of 17 (25 mg, 32 µmol) in 80% aq. AcOH (1.0 ml) and dioxane (0.8 ml) was treated with 20% Pd(OH)₂/C (25 mg) and stirred under H₂ (1 atm) for 15 h. The mixture was filtered through Celite, washing with H₂O. The combined filtrate and washings were evaporated. A solution of the residue in H₂O was washed with CH₂Cl₂. Lyophilisation of the aq. solution gave 18·4AcOH=ETH 102 (25.6 mg, 90%), white fluffy solid. IR (ATR): 3205m (br.), 1633m, 1540s, 1404s, 1339m, 1131s (sh.), 1102s, 996s. ¹H-NMR (500 MHz, D₂O): 5.66 (d, J=3.5, H—C(1')); 5.44 (d, J=3.9, H—C(1")); 5.16 (d, J=8.5, H—C(8')); 4.54 (t, J=1.7, H—C(6')); 4.28 (dd, J=7.8, 4.1, CH(OH)CH₂CH₂); 3.96 (t, J=10.3, H—C(3"), H—C(5")); 3.89 (td, J=10.8, 6.8, H—C(3)); 3.85-3.72 (m, H—C(6), H—C(5')); 3.67-3.58 (m, H—C(4), H—C(2'), H—C(4'), H—C(2"), H—C(6")); 3.50 (t, J=9.8, H—C(5)); 3.43-3.37 (m, H—C(1)); 3.33 (dd, J=8.4, 2.5, H—C(7')); 3.13-3.08 (m, H—C(4"), CH(OH)CH₂CH₂); 2.76 (s, NMe); 2.34 (dt, J=10.8, 5.0, CH(OH)CH$_a$CH₂); 2.20 (dt, J=12.9, 4.2, $H_{eq}$—C(2)); 2.17-2.08 (m, $H_{eq}$—C(a)); 2.03-1.92 (m, CH(OH)CH$_b$CH₂), $H_{ax}$—C(a)); 1.71 (q, J=12.7, $H_{ax}$—C(2)). ¹³C-NMR (125 MHz, D₂O): 181.30 (s, MeCO₂H); 175.61 (s, C=O); 95.77 (d, C(1')); 94.65 (d, C(1")); 93.11 (d, C(8')); 75.87 (d, C(4)); 73.78 (d, C(5)); 70.51 (d, C(2")); 69.74-69.54 (several d, C(6), C(4'), C(5'), C(4"), C(5"), CH(OH)CH$_2$CH$_2$); 66.15 (d, C(3")); 62.93 (d, C(6')); 60.54 (t, C(6")); 59.56 (d, C(7')); 52.23 (d, C(4")); 49.06 (d, C(1)); 48.78 (d, C(3)); 48.12 (d, C(2')); 36.58 (t, CH(OH)CH$_2$CH$_2$); 30.89 (t, C(2)); 30.70 (t, C(3')); 30.27 (q, NMe); 27.24 (t, CH(OH)CH$_2$CH$_2$); 23.29 (MeCO$_2$H). HR-MALDI-MS: 663.3180 (24, [M+Na]$^+$, C$_{25}$H$_{48}$N$_6$NaO$_{13}$$^+$; calc. 663.3177), 641.3363 (52, [M+H]$^+$, C$_{25}$H$_{49}$N$_6$O$_{13}$$^+$; calc. 641.3358).

3,2'-Bis-N-[(2S)-4-(benzyloxycarbonylamino)-2-hydroxybutyryl]apramycin (19) and 2'-N-[(2S)-4-(benzyloxycarbonylamino)-2-hydroxybutyryl]apramycin (20)

A solution of 1 (200 mg, 0.37 mmol) in 1:4 H$_2$O/DMF (25 ml) was treated with nickel(II) acetate tetrahydrate (369 mg, 1.48 mmol, see Kirst et al., *Tet. Lett.* 1981, 22:295; Allen et al., *J. Med. Chem.* 1987, 30:333) and stirred for 1 h. The mixture was treated with N-[(2S)-4-(benzyloxycarbonylamino)-2-hydroxybutyryl]succinimide (16; 194 mg, 0.55 mmol) and stirred for 15 h at 26° C. After evaporation of the solvents, the residue was dissolved in CHCl$_3$/MeOH/aq. NH$_3$ (25%) 3:3:1 and pre-adsorbed on silicagel. FC(CHCl$_3$/MeOH/aq. NH$_3$ (25%) 10:10:1→3:3:1→0:4:1) and lyophilisation gave 19 (37 mg, 10%) and 20 (129 mg, 45%). Data of 19: White fluffy solid. R$_f$ (MeOH/25% aq. NH$_3$ 4:1) 0.42. IR (ATR): 3242w (br.), 2940w, 1692w, 1646w, 1532w, 1455w, 1341w, 1267w, 1054s, 1033s, 1000s, 860w, 735m, 697m. $^1$H-NMR (400 MHz, D$_2$O): 7.41-7.32 (m, 10H arom.); 5.40, 5.38 (2 d, J=3.7, H—C(1'), H—C(1")); 5.10 (d, J=8.5, H—C(8')); 5.05 (t, J=10.6, 2PhCH$_2$); 4.50 (t, J=2.6, H—C(6')); 4.18-4.12 (m, 2CH(OH)CH$_2$CH$_2$); 4.07-3.34 (m, 12H); 3.28-3.14 (m, H—C(7'), 2CH(OH)CH$_2$CH$_2$); 3.06-2.98 (m, 1H); 2.73 (s, NMe); 2.42-2.30 (m, 2CH(OH)—CH$_a$CH$_2$); 2.14-2.02 (m, H$_{eq}$—C(2)); 1.98-1.88 (m, 2H); 1.84-1.69 (m, 2H); 1.66-1.56 (m, H$_{ax}$—C(2)). HR-MALDI-MS: 1032.4340 (63, [M+Na]$^+$, C$_{45}$H$_{67}$N$_7$NaO$_{19}$$^+$; calc. 1032.4349), 1010.4579 (100, [M+H]$^+$, C$_{45}$H$_{68}$N$_7$O$_{19}$$^+$; calc. 1010.4570). Data of 20: White solid. R$_f$ (MeOH/25% aq. NH$_3$ 4:1) 0.15. IR (ATR): 3280w (br.), 2944w, 1692w, 1644w, 1531w, 1454w, 1337w, 1265w, 1058s, 1033s, 1000s, 858w, 735m, 695m. $^1$H-NMR (400 MHz, D$_2$O): 7.44-7.35 (m, 5H arom.); 5.50 (d, J=3.0, H—C(1')); 5.43 (d, J=3.9, H—C(1")); 5.15 (d, J=8.5, H—C(8')); 5.07 (br. s, PhCH$_2$); 4.58 (t, J=2.6, H—C(6')); 4.15 (dd, J=7.7, 4.5, CH(OH)CH$_2$CH$_2$); 4.11-4.03 (m, H—C(2'), H—C(3"), H—C(5")); 3.88-3.78 (m, H—C(4), H—C(4'), 2H—C(6")); 3.68-3.63 (m, H—C(5'), H—C(2")); 3.55 (q, J=9.4, H—C(5), H—C(6)); 3.47-3.40 (m, H—C(3)); 3.37 (dd, J=8.6, 2.8, H—C(7')); 3.29-3.21 (m, H—C(1), H—C(4"), CH(OH)CH$_2$CH$_2$); 2.82 (s, NMe); 2.48 (dt, J=12.6, 6.6, H$_{eq}$—C(2)); 2.10-2.04 (m, H$_{eq}$—C(3')); 2.04-1.75 (m, H$_{ax}$—C(2), H$_{ax}$—C(3'), CH(OH)CH$_2$CH$_2$). $^{13}$C-NMR (100 MHz, D$_2$O): 175.48 (s, (OH)CHC=O); 158.31 (s, C=O); 136.52 (s, arom.); 128.86, 128.45, 127.70 (3 d, arom.); 96.68 (d, C(1')); 94.50 (d, C(1")); 92.83 (d, C(8')); 75.40 (d); 72.74 (d); 70.52 (d); 69.80, 69.46, 69.17 (3 d); 68.28 (d); 66.81 (t, PhCH$_2$); 62.85 (d); 60.51 (t, C(6")); 59.50 (d); 52.27 (d); 49.86 (d); 49.15 (d); 47.11 (d); 36.60 (t, CH(OH)CH$_2$CH$_2$); 33.37 (t, CH(OH)CH$_2$CH$_2$); 30.18 (q, NMe); 28.44 (t, C(2)); 28.21 (t, C(3')). HR-MALDI-MS: 797.3538 (63, [M+Na]$^+$, C$_{33}$H$_{54}$N$_6$NaO$_{15}$$^+$; calc. 797.3545), 775.3707 (100, [M+H]$^+$, C$_{33}$H$_{55}$N$_6$O$_{15}$$^+$; calc. 775.3725)

3,2'-Bis-N-[(2S)-4-amino-2-hydroxybutyryl]apramycin tetraacetate (21=ETH 101)

A solution of 19 (10 mg, 9.9 μmol) in 80% aq. AcOH (1.0 ml) and dioxane (0.8 ml) was treated with 20% Pd(OH)$_2$/C (10 mg) and stirred under H$_2$ (1 atm) for 15 h. The mixture was filtered through Celite, washing with H$_2$O. The combined filtrate and washings were evaporated. A solution of the residue in H$_2$O was washed with CH$_2$Cl$_2$. Lyophilisation of the aq. solution gave 21'·4AcOH=ETH 101 (7.8 mg, 80%), white solid. IR (ATR): 3205m (br.), 2936m, 1641s, 1550s, 1406s, 1341m, 1268w, 1099s, 1056s, 1014s, 994s, 862w. $^1$H-NMR (600 MHz, D$_2$O): 5.52 (d, J=4.2, H—C(1')); 5.46 (d, J=3.6, H—C(1")); 5.21 (d, J=9.0, H—C(8')); 4.60 (br. s, H—C(6')); 4.36-4.29 (m, 2CH(OH)CH$_2$CH$_2$); 4.19-3.27 (m, 13H); 3.21-3.09 (m, 2CH(OH)CH$_2$CH$_2$); 2.81 (s, NMe); 2.50-2.42 (m, 1H); 2.24-2.11 (m, 3H); 2.07-1.94 (m, 3H); 1.92 (s, MeCO$_2$H); 1.80-1.72 (m, 1H). HR-MALDI-MS: 764.3680 (23, [M+Na]$^+$, C$_{29}$H$_{55}$N$_7$NaO$_{15}$$^+$; calc. 764.3657), 742.3837 (100, [M+H]$^+$, C$_{25}$H$_{49}$N$_6$O$_{13}$$^+$; calc. 742.3834)

2'-N-[(2S)-4-Amino-2-hydroxybutyryl]apramycin tetraacetate (22=ETH 100)

A solution of 20 (25 mg, 32.3 μmol) in 80% aq. AcOH (1.0 ml) and dioxane (0.8 ml) was treated with 20% Pd(OH)$_2$/C (25 mg) and stirred under H$_2$ (1 atm) for 15 h. The mixture was filtered through Celite, washing with H$_2$O. The combined filtrate and washings were evaporated. A solution of the residue in H$_2$O was washed with CH$_2$Cl$_2$. Lyophilisation of the aq. solution gave 22'·4AcOH=ETH 100 (25.6 mg, 90%). IR (ATR): 3178w (br.), 3067w, 2940w, 1631w, 1531w, 1462w, 1407w, 1331w, 1274w, 1045s, 994s, 973w (sh.), 863w. $^1$H-NMR (600 MHz, D$_2$O): 5.42 (d, J=3.7, H—C(1')); 5.37 (d, J=3.9, H—C(1")); 5.09 (d, J=8.5, H—C(8')); 4.50 (t, J=2.4, H—C(6')); 4.20 (dd, J=8.5, 4.0, CH(OH)CH$_2$CH$_2$); 4.05 (dt, J=12.8, 4.1, H—C(2')); 3.99 (t, J=12.0, H—C(3"), H—C(5")); 3.84 (td, J=10.8, 4.3, H—C(4')); 3.77-3.74 (m, 2H—C(6")); 3.70 (dd, J=15.0, 5.4, H—C(5')); 3.62 (dd, J=10.0, 2.3, H—C(4)); 3.57 (dd, J=9.8, 3.9, H—C(2")); 3.52 (dd, J=9.8, 8.2, H—C(5)); 3.48 (t, J=9.7, H—C(6)); 3.39 (ddd, J=15.5, 12.6, 4.8, H—C(3)); 3.29 (dd, J=8.6, 2.7, H—C(7')); 3.22 (ddd, J=12.3, 10.1, 4.1, H—C(1)); 3.15 (t, J=10.3, H—C(4")); 3.04 (t, J=7.5, CH(OH)CH$_2$CH$_2$); 2.73 (s, NMe); 2.40 (dt, J=12.6, 4.2, H$_{eq}$—C(2)); 2.08-2.00 (m, H$_{eq}$—C(3'), CH(OH)CH$_a$CH$_2$); 1.91-1.76 (m, H$_{ax}$—C(2), H$_{ax}$—C(3'), CH(OH)CH$_b$CH$_2$)); 1.79 (s, MeCO$_2$H). $^{13}$C-NMR (150 MHz, D$_2$O): 174.58 (s, C=O); 96.60 (d, C(1')); 94.27 (d, C(1")); 92.63 (d, C(8')); 78.40, 75.02, 72.40 (3 d, C(5), C(6), C(2")); 70.23 (d, C(4)); 69.58, 69.27, 69.21 (3 d, C(5'), C(5"), CH(OH)CH$_2$CH$_2$); 67.97 (d, C(3")); 66.62 (d, C(4')); 62.58 (d, C(6')); 60.17 (t, C(6")); 59.21 (d, C(7')); 51.92. (d, C(4")); 49.61 (d, C(1)); 48.89 (d, C(3)); 46.91 (d, C(2')); 36.49 (t, CH(OH)CH$_2$CH$_2$); 30.59 (t, CH(OH)CH$_2$CH$_2$); 29.86 (q, NMe); 28.14 (t, C(2)); 27.92 (t, C(3')). HR-MALDI-MS: 663.3147 (53, [M+Na]$^+$, C$_{25}$H$_{48}$N$_6$NaO$_{13}$$^+$; calc. 663.3177), 641.3339 (100, [M+H]$^+$, C$_{25}$H$_{49}$N$_6$O$_{13}$$^+$; calc. 641.3358).

Example 12

Activity of Apramycin Derivatives for Various Ribosomes (Table 10)

Activity was assessed by determination of minimal inhibitory concentrations (MIC) as described in Example 1. For further detail on methodology see description in Example 7. The results are shown in Table 10.

TABLE 10

MIC determination (µg/ml) of apramycin derivatives

| | wild type bacteria | bacteria with cytohybrid ribosome | bacteria with mitohybrid ribosome | bacteria with deafness 1555G ribosome | bacteria with deafness 1494U ribosome |
|---|---|---|---|---|---|
| Apramycin | 1.0-2.0 | >256.0 | >256.0 | >256.0 | >256.0 |
| ETH 99 | 2.0-4.0 | >256.0 | >256.0 | n.d. | n.d. |
| ETH 100 | 2.0-4.0 | >256.0 | >256.0 | >256.0 | >256.0 |
| ETH 102 | 4.0 | >256.0 | >256.0 | >256.0 | >256.0 |
| ETH 103 | 8.0 | >256.0 | >256.0 | >256.0 | >256.0 |
| ETH 105 | 4.0 | >256.0 | >256.0 | >256.0 | >256.0 |

The invention claimed is:

1. A method of treatment of bacterial infectious diseases in humans, comprising administering to a patient in need thereof, an effective amount of an apramycin derivative or an acid addition salt thereof of formula (II),

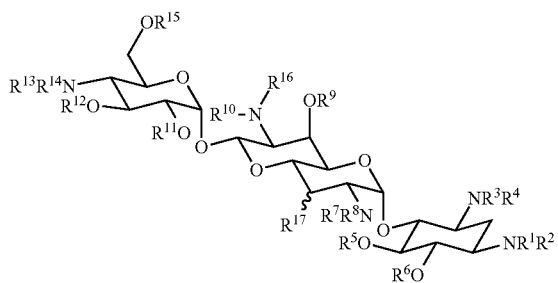

(II)

wherein $R^1$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^2$ is hydrogen, $C_1$-$C_4$-alkyl, or $C_1$-$C_4$-alkenyl;

$R^3$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^4$ is hydrogen, $C_1$-$C_4$-alkyl, or $C_1$-$C_4$-alkenyl;

$R_5$ is hydrogen, $C_1$-$C_4$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^6$ is hydrogen, $C_1$-$C_4$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^1$ and $R^6$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O; or $R^5$ and $R^6$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^7$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_4$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^8$ is hydrogen, $C_1$-$C_4$-alkyl, or $C_1$-$C_4$-alkenyl;

$R^9$ is hydrogen, $C_1$-$C_4$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$;

$R^{10}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^9$ and $R^{10}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{11}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxyl-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$ or $PO(OH)_2$;

$R^{12}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_4$-alkenyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{11}$ and $R^{12}$ together represent $C_1$-$C_7$-acyl-CH, phenyl-CH, $(C_1$-$C_7$-alkyl$)_2$C, cyclo-$(CH_2)_4$C, cyclo-$(CH_2)_5$C, or C=O;

$R^{13}$ is hydrogen, $C_1$-$C_7$-alkyl, cyclopropylmethyl, optionally substituted benzyl, amino-$C_1$-$C_7$-alkyl, acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_3$-$C_7$-cycloalkyl, $C_1$-$C_4$-alkenyl, $C_1$-$C_7$-acyl, amino-$C_1$-$C_7$-acyl, acetylamino-$C_1$-$C_7$-acyl, hydroxyl-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{12}$ and $R^{13}$ together represent $C_1$-$C_7$-alkyl-CH, phenyl-CH, $(C_1$-$C_7$-alkyl$)_2$C, cyclo-$(CH_2)_4$C, cyclo-$(CH_2)_5$C, or C=O;

$R^{14}$ is hydrogen, $C_1$-$C_4$-alkyl, or $C_1$-$C_4$-alkenyl; or $R^{15}$ is hydrogen, $C_1$-$C_7$-alkyl, cyclopropylmethyl, optionally substituted benzyl, amino-acetylamino-$C_1$-$C_7$-alkyl, hydroxy-$C_1$-$C_7$-alkyl, amino-hydroxy-$C_1$-$C_7$-alkyl, acetylamino-hydroxy-$C_1$-$C_7$-alkyl, $C_1$-$C_7$-acyl, amino-$C_1$-$C_7$-acyl, acetylamino-$C_1$-$C_7$-acyl, hydroxy-$C_1$-$C_7$-acyl, amino-hydroxy-$C_1$-$C_7$-acyl, acetylamino-hydroxy-$C_1$-$C_7$-acyl, aminoacetyl derived from the 20 naturally occurring essential α-amino acids, aroyl, heteroaroyl, $SO_2OH$, or $PO(OH)_2$; or $R^{13}$ and $R^{15}$ together represent $C_1$-$C_7$-alkyl-CH, phenyl-CH, $(C_1$-$C_7$-alkyl$)_2$C, $(CH_2)_4$C, $(CH_2)_5$C, or C=O;

$R^{16}$ is hydrogen, $C^1$-$C^4$-alkyl, cyclopropylmethyl, cyclopropyl, or $C_1$-$C_4$-alkenyl; or N—$R^{10}$ and $R^{16}$ together represent a saturated or partially unsaturated heterocycle; and $R^{17}$ is hydrogen; amino, $C_1$-$C_7$-alkylamino, cyclopropylmethylamino, optionally substituted benzylamino, amino-$C_1$-$C_7$-alkylamino, acetylamino-$C_1$-$C_7$-alkylamino, hydroxy-$C_1$-$C_7$-alkylamino, amino-hydroxy-$C_1$-$C_7$-alkylamino, acetylamino-hydroxy-$C_1$-$C_7$-alkylamino, $C_3$-$C_7$-cycloalkylamino, $C_1$-$C_4$-alkenylamino, $C_1$-$C_7$-acylamino, amino-$C_1$-$C_7$-acylamino, acetylamino-$C_1$-$C_7$-acylamino, hydroxy-$C_1$-$C_7$-acylamino, amino-hydroxy-$C_1$-$C_7$-acylamino, acetylamino-hydroxy-$C_1$-$C_7$-acylamino, aminoacetylamino, wherein aminoacetyl is derived from the 20 naturally occurring essential α-amino acids, aroylamino, heteroaroylamino, $NHSO_2OH$, $NHPO(OH)_2$; hydroxy, $C_1$-$C_7$-alkoxy, cyclopropylmethoxy, optionally substituted benzyloxy, amino-$C_1$-$C_7$-alkoxy, acetylamino-$C_1$-$C_7$-alkoxy, hydroxy-$C_1$-$C_7$-alkoxy, amino-hydroxy-$C_1$-$C_7$-alkoxy, acetylamino-hydroxy-$C_1$-$C_7$-alkoxy, $C_1$-$C_4$-alkenyloxy, $C_1$-$C_7$-acyloxy, amino-$C_1$-$C_7$-acyloxy, acetylamino-$C_1$-$C_7$-acyloxy, hydroxy-$C_1$-$C_7$-acyloxy, amino-hydroxy-$C_1$-$C_7$-acyloxy, acetylamino-hydroxy-$C_1$-$C_7$-acyloxy, aminoacetoxy wherein aminoacetyl is derived from the 20 naturally occurring essential α-amino acids, aroyloxy, heteroaroyloxy, $OSO_2OH$, or $OPO(OH)_2$; with the proviso, that when $R^{16}$ is methyl and $R^{17}$ is hydrogen, at least one of the substituents $R^1$ to $R^{15}$ is different from hydrogen; derivatives thereof, wherein one or more amino group are in protected form; or a pharmaceutically acceptable acid addition salt thereof.

2. The method of treatment according to claim 1, wherein the acid addition salt of apramycin is a pharmaceutically acceptable acid addition salt.

3. The method of treatment according to claim 1, of bacterial infectious diseases in humans comprising administering to a patient in need thereof an effective amount of apramycin of formula (II) or of a pharmaceutically acceptable acid addition salt thereof.

4. The method of treatment according to claim 1, wherein the apramycin derivative or the acid addition salt thereof is of formula (II), wherein $R^1$ or $R^7$ or $R^{13}$ is amino-, acetylamino- and/or hydroxy-$C_1$-$C_7$-acyl, $R^{16}$ is methyl, and all other substituents are hydrogen.

5. The method of treatment according to claim 1, wherein the apramycin derivative or the acid addition salt thereof is of formula (II), wherein $R^9R^{10}$ is C=O, $R^{13}$ is amino-, acetylamino- and/or hydroxy-$C_1$-$C_7$-acyl, $R^{16}$ is methyl, and all other substituents are hydrogen.

6. The method of treatment according to claim 1, wherein the infectious disease is tuberculosis or an infectious disease caused by non-tuberculous mycobacteria.

7. The method of treatment according to claim 1, wherein the infectious disease is pneumonia due to *Pseudomonas* spp. infection in cystic fibrosis patients, or disseminated infection to *Francisella tularensis, Rickettsia* spp., *Brucella* spp., *Enteribacteriaceae* spp., and *Pseudomonas* spp.

8. The method of treatment according to claim 1, wherein the apramycin, apramycin derivative, or acid addition salt thereof is administered intravenously or subcutaneously.

9. The method of treatment according to claim 1, wherein the apramycin, apramycin derivative, or acid addition salt thereof is administered in a daily dose from 1 mg/kg to 25 mg/kg bodyweight.

10. The method of treatment according to claim 1, wherein the apramycin, apramycin derivative, or acid addition salt thereof is administered as an aerosol.

11. A method of treatment of bacterial infectious diseases in humans, comprising administering to a patient in need thereof, an effective amount of an apramycin derivative formula (II),

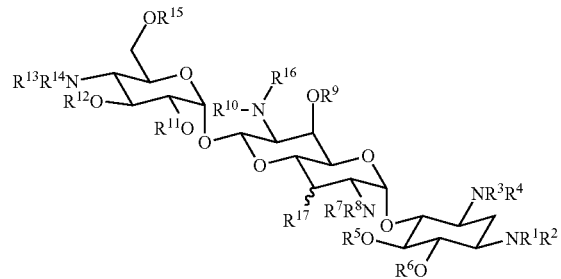

(II)

wherein
$R^1$ is γ-amino-α-hydroxybutyryl and all other substituents are hydrogen;
$R^7$ γ-amino-α-hydroxybutyryl and all other substituents are hydrogen; or
$R^9R^{10}$ together represent C=O, $R^{13}$ is γ-amino-α-hydroxybutyryl and all other substituents are hydrogen.

12. A method of treatment of bacterial infectious diseases in humans, comprising administering to a patient in need thereof, an effective amount of an apramaycin derivative formula (II),

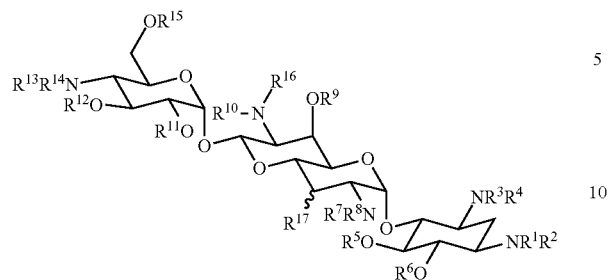
(II)
wherein
- $R^{10}$ is allyl, $R^{16}$ is methyl, and all other substituents are hydrogen;
- $R^{16}$ is ethyl, and all other substituents are hydrogen;
- $R^{16}$ is cyclopropylmethyl, and all other substituents are hydrogen;
- $R^{16}$ is cyclopropyl, and all other substituents are hydrogen; or
- $R^{16}$ is allyl, and all other substituents are hydrogen.
* * * * *

UNITED STATES PATENT AND TRADEMARK OFFICE
CERTIFICATE OF CORRECTION

PATENT NO. : 9,271,993 B2  
APPLICATION NO. : 13/820258  
DATED : March 1, 2016  
INVENTOR(S) : Boettger Page 1 of 1

It is certified that error appears in the above-identified patent and that said Letters Patent is hereby corrected as shown below:

Claims col. 29, line 61, claim 1: replace "$R_5$" with "$R^5$"

col. 31, line 26, claim 1: after "amino-" and before "$C_1$-$C_7$" delete "acetylamino-"

col. 31 line 27, claim 1: after "alkyl," and before "hydroxyl-$C_1$-$C_7$-alkyl," insert --acetylamino-$C_1$-$C_7$-alkyl,-- col. 31, line 28, claim 1: after "acetylamino-hydroxy- $C_1$-$C_7$-alkyl," and before "hydroxy-" insert --$C_1$-$C_4$-alkenyl,-- col. 31, line 36, claim 1: replace "$C^1$-$C^4$" with "$C_1$-$C_4$"

col. 31, line 40, claim 1: after "hydrogen" replace ";" with ","

col. 31, line 52, claim 1: after "$NHPO(OH)_2$" replace ";" with ","

col. 31, line 63, claim 1: after "$OPO(OH)_2$" replace ";" with ","

col. 31, line 65, claim 1: after "hydrogen" replace ";" with ","

Signed and Sealed this  
Twenty-sixth Day of July, 2016

Michelle K. Lee  
*Director of the United States Patent and Trademark Office*